US011359010B2

(12) United States Patent
Tessier et al.

(10) Patent No.: US 11,359,010 B2
(45) Date of Patent: Jun. 14, 2022

(54) HUMANIZED ANTI-S100A9 ANTIBODY AND USES THEREOF

(71) Applicant: UNIVERSITÉ LAVAL, Québec (CA)

(72) Inventors: Philippe Tessier, Montréal (CA); Mélanie Tardif, Quebec (CA); Traian Sulea, Kirkland (CA)

(73) Assignee: UNIVERSITÉ LAVAL, Québec (CA)

( * ) Notice: Subject to any disclaimer, the term of this patent is extended or adjusted under 35 U.S.C. 154(b) by 811 days.

(21) Appl. No.: 16/316,146

(22) PCT Filed: Jul. 11, 2016

(86) PCT No.: PCT/CA2016/050810
§ 371 (c)(1),
(2) Date: Jan. 8, 2019

(87) PCT Pub. No.: WO2017/008153
PCT Pub. Date: Jan. 19, 2017

(65) Prior Publication Data
US 2021/0277101 A1    Sep. 9, 2021

Related U.S. Application Data

(60) Provisional application No. 62/191,733, filed on Jul. 13, 2015.

(51) Int. Cl.
*C07K 16/24* (2006.01)
*A61K 9/00* (2006.01)

(52) U.S. Cl.
CPC ............ *C07K 16/24* (2013.01); *A61K 9/0019* (2013.01); *C07K 2317/24* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| 6,180,370 B1 * | 1/2001 | Queen | A61P 31/12 435/69.6 |
| 8,282,925 B2 * | 10/2012 | Tessier | A61P 35/02 424/152.1 |
| 2014/0343256 A1 * | 11/2014 | Kirschning | A61P 31/04 530/387.3 |

FOREIGN PATENT DOCUMENTS

| CN | 102712681 A | 10/2012 |
| WO | 2011057101 | 5/2011 |

OTHER PUBLICATIONS

Cesaro, Annabelle, et al. "An inflammation loop orchestrated by S100A9 and calprotectin is critical for development of arthritis." (2012): e45478. (Year: 2012).*
Cesaro, Annabelle et al. PloS one vol. 7,9 (2012): e45478. doi: 10.1371/journal.pone.0045478 (Year: 2012).*
Janeway, Charles A. "Immunobiology: The Immune System in Health and Disease." 2005 (Year: 2005).*
Defrêne, Joan, et al. The Journal of Immunology 206.3 (2021): 505-514 (Year: 2021).*
Rousseau, Louis-Simon, et al. Journal of leukocyte biology 102.3 (2017): 805-813 (Year: 2017).*
Zhang, Xuemei et al. Frontiers in immunology vol. 8 1774. Dec. 13, 2017, doi:10.3389/fimmu.2017.01774 (Year: 2017).*
Lee, Tae-Hyeong, et al. Clinical Immunology 183 (2017): 158-166 (Year: 2017).*
Dand et al, J Immunol May 1, 2017, 198 1 Supplement. 207.3 (Year: 2017).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Mistry et al. "Inhibition of TLR2 signaling by small molecule inhibitors targeting a pocket within the TLR2 TIR domain", Proceeding of the National Academy of Sciences, vol. 112, No. 17, 2015, pp. 5455-5460.
Cesaro et al. "An inflammation loop orchestrated by S100A9 and calprotectin is critical for development of arthritis". PLoS ONE. Sep. 2012, vol. 7, No. 9, 1932-6203.
Moles et al."A TLR2/S100A9/CXCL-2 signaling network is necessary for neutrophil recruitment in acute and chronic iver injury in the mouse" Journal of Hepatology, Apr. 2014, vol. 60, No. 4, pp. 782-791.
English Translated Abstract of CN102712681A.

* cited by examiner

*Primary Examiner* — Michael Szperka
*Assistant Examiner* — Lia E Taylor
(74) *Attorney, Agent, or Firm* — Norton Rose Fulbright Canada LLP

(57) ABSTRACT

It is provided an inhibitor of Toll-like Receptor 2 (TLR2) that specifically blocks an interaction between S1009A and Toll-like Receptor 2 (TLR2), and more particularly a humanized antibody against S100A9 protein for inhibiting and treating inflammatory conditions in a human patient. Particularly, this humanized antibody is specific for blocking the interaction between the S100A9 protein and the TLR-2 receptor.

7 Claims, 17 Drawing Sheets
Specification includes a Sequence Listing.

(1): 1 residue = an N-terminal semi-buried residue (N2) with antigen-contact propensity and part of Vernier zone (2): 4 residues = variant (1) + buried residue (W47) from Vernier zone supporting CDR-L1 also with proximal R45)

(3): 6 residues = variant (2) + 2 residues (K69 and buried V71 also with antigen-contacting propensity) from the Vernier zone under CDR-H1

(4): 8 residues = variant (3) + a heavy chain proximal residue (S43) and a residue whose mutation modifies surface charge close to CDR-L

Figure 5D

| Positional preference in variable domain of human heavy chains |||||||
|---|---|---|---|---|---|---|
| Position | Residue | Residue | Residue | Residue | Residue | Residue |
| 1=1 | E 44% | Q 54% | T 2% | | | |
| 5=5 | V 72% | Q 20% | K 2% | L 2% | | |
| 6=6 | Q 30% | E 70% | | | | |
| 7=7 | S 87% | T 13% | | | | |
| 9=10 | G 48% | D 24% | A 22% | S 2% | | |
| 11=12 | L 67% | V 33% | | | | |
| 12=13 | V 70% | K 26% | L 2% | | | |
| 13=14 | K 55% | L 22% | P 20% | T 1% | | |
| 20=21 | L 71% | V 22% | I 5% | | | |
| 38=45 | R 93% | Q 4% | R 0% | | | |
| 40=47 | P 21% | A 7% | | | | |
| 44=51 | G 89% | A 7% | R 4% | | | |
| 48=55 | W 48% | I 25% | L 20% | | | |
| 66=77 | R 95% | M 1% | | | | |
| 67=78 | F 53% | V 40% | A 0% | | | |
| 69=90 | T 84% | M 11% | F 4% | | | |
| 71=92 | R 60% | W 10% | | | | |
| 73=94 | S 40% | T 38% | I 17% | | | |
| 75=86 | K 67% | T 13% | P 20% | S 0% | | |
| 76=89 | L 44% | A 29% | M 18% | W 7% 50% | | |
| 81=92 | Q 55% | R 18% | M 15% | | | |
| 83=97 | R 56% | T 22% | S 0% | | | |
| 87=101 | T 89% | M 11% | V 5% | | | |
| 93=107 | A 87% | V 5% | W 5% | S 0% | | |

Figure 6C

Legend of human sequences in the same order as in the alignment:
Consensus human hv1
>gb|ABA10037.1|
emb|CAB43243.1| emb|CAC06621.1| emb|CAC06627.1|
gb|AAD30405.1|AF115119_1
gb|AAW08086.1|
gb|ABM67127.1|
num|ChV212 IGHV1-46*03, IGHV1-46*01, VH1-46, DP-7/V1-2,...,t,
num|CHV74 294 bp
num|CHV33 IGHV1-46*02, HC34 294 bp
xConsensus human hv1
pdb|1I9R|H (hmzd)
pdb|1MFP|H pdb|3KE3|H (hmzd)
pdb|1U0J|B (hmzd)
pdb|1GKW|H (hmzd)
pdb|1WT3|A (hmzd)

5 - close to CDRs (<5 Å)
b - buried
v - Vernier zone
h - contact to heavy chain
l - contact to light chain
c - contact to constant region

SEQUENCE LISTING

<160> NUMBER OF SEQ ID NOS: 76

<210> SEQ ID NO 1
<211> LENGTH: 106
<212> TYPE: PRT
<213> ORGANISM: Artificial Sequence
<220> FEATURE:
<223> OTHER INFORMATION: V domain of the light chain of mouse anti-
      S100A9

<400> SEQUENCE: 1

Glu Asn Val Leu Thr Gln Ser Pro Ala Ile Met Ser Ala Ser Pro Gly
1               5                   10                  15

Glu Lys Val Thr Met Thr Cys Ser Ala Arg Ser Ser Val Ser Tyr Val
                20                  25                  30

His Trp Tyr Gln Gln Lys Ser Asn Thr Ser Pro Lys Leu Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Leu Lys
            100                 105

<210> SEQ ID NO 2
<211> LENGTH: 106
<212> TYPE: PRT
<213> ORGANISM: Artificial Sequence
<220> FEATURE:
<223> OTHER INFORMATION: 6B4-VL_humanized-1

<400> SEQUENCE: 2

Glu Asn Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Val
                20                  25                  30

His Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Gln Gly Thr Lys Leu Glu Ile Lys
            100                 105

<210> SEQ ID NO 3
<211> LENGTH: 107
<212> TYPE: PRT
<213> ORGANISM: Artificial Sequence
<220> FEATURE:
<223> OTHER INFORMATION: V domain of the light chain of humanized anti-
      6B4

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Ser Asp Asn
                85                  90                  95

Thr Phe Gly Gln Gly Thr Lys Leu Glu Ile Lys
            100                 105

<210> SEQ ID NO 4
<211> LENGTH: 107
<212> TYPE: PRT
<213> ORGANISM: Artificial Sequence
<220> FEATURE:
<223> OTHER INFORMATION: V domain of the light chain of humanized anti-6B4

<400> SEQUENCE: 4

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Ser Asp Asn
                85                  90                  95

Thr Phe Gly Gln Gly Thr Lys Leu Glu Ile Lys
            100                 105

<210> SEQ ID NO 5
<211> LENGTH: 107
<212> TYPE: PRT
<213> ORGANISM: Artificial Sequence
<220> FEATURE:
<223> OTHER INFORMATION: V domain of the light chain of humanized anti-6B4

<400> SEQUENCE: 5

Glu Asn Val Leu Thr Gln Ser Pro Ala Thr Leu Ser Leu Ser Pro Gly
 1               5                  10                  15

Asp Arg Ala Thr Leu Ser Cys Arg Ala Thr Gln Ser Val Asn Arg Ser
            20                  25                  30

Leu Gly Trp Phe Gln Gln Lys Gly Gly Gln Ala Pro Arg Leu Leu Ile
            35                  40                  45

Tyr Asp Ser Phe Lys Arg Ala Ala Gly Val Pro Ala Arg Phe Ser Gly
 50                  55                  60

Ser Gly Ser Gly Thr Asp Phe Thr Leu Thr Ile Ser Thr Leu Glu Pro
 65                  70                  75                  80

Glu Asp Phe Ala Val Tyr Tyr Cys Gln His Cys Arg Asn Gly Leu Val
                85                  90                  95

Thr Phe Gly Gln Gly Thr Arg Leu Glu Ile Lys
            100                 105

<210> SEQ ID NO 6
<211> LENGTH: 107
<212> TYPE: PRT
<213> ORGANISM: Artificial Sequence
<220> FEATURE:
<223> OTHER INFORMATION: V domain of the light chain of humanized anti-6B4

<400> SEQUENCE: 6

Glu Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Leu Glu Ile Lys
            100                 105

<210> SEQ ID NO 7
<211> LENGTH: 107
<212> TYPE: PRT
<213> ORGANISM: Artificial Sequence
<220> FEATURE:
<223> OTHER INFORMATION: V domain of the light chain of humanized anti-6B4

<400> SEQUENCE: 7

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Thr Phe Gly Gln Gly Thr Lys Leu Glu Ile Lys
            100                 105

<210> SEQ ID NO 8
<211> LENGTH: 105
<212> TYPE: PRT
<213> ORGANISM: Artificial Sequence
<220> FEATURE:
<223> OTHER INFORMATION: V domain of the light chain of humanized anti-6B4

<400> SEQUENCE: 8

Val Met Thr Gln Ser Pro Ser Ser Leu Ser Ala Ser Val Gly Glu Arg

```
                1               5                  10                 15
Val Thr Ile Thr Cys Arg Ala Ser Gln Gly Ile Asn Asn Tyr Val Ala
                20                 25                 30

Trp Tyr Gln Gln Lys Pro Gly Lys Val Pro Lys Leu Leu Ile Tyr Ala
                35                 40                 45

Ala Ser Ser Leu Gln Ser Gly Val Pro Ser Arg Phe Ser Gly Ser Gly
                50                 55                 60

Ser Gly Thr Glu Phe Thr Leu Thr Ile Ser Ser Leu Gln Ala Glu Asp
65                 70                 75                 80

Val Ala Thr Tyr Tyr Cys Gln Lys Tyr Asp Ser Ala Pro Arg Thr Phe
                85                 90                 95

Gly Gln Gly Thr Arg Val Glu Ile Lys
                100                105

<210> SEQ ID NO 9
<211> LENGTH: 107
<212> TYPE: PRT
<213> ORGANISM: Artificial Sequence
<220> FEATURE:
<223> OTHER INFORMATION: V domain of the light chain of humanized anti-
      6B4

<400> SEQUENCE: 9

Glu Ile Val Leu Thr Gln Ser Pro Ser Leu Ser Ala Ser Val Gly
1               5                  10                 15

Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
                35                 40                 45

Tyr Ala Ala Ser Ser Leu Gln Ser Gly Val Pro Ser Arg Phe Ser Gly
                50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Thr Pro Tyr
                85                 90                 95

Thr Phe Gly Gln Gly Thr Lys Leu Glu Ile Lys
                100                105

<210> SEQ ID NO 10
<211> LENGTH: 107
<212> TYPE: PRT
<213> ORGANISM: Artificial Sequence
<220> FEATURE:
<223> OTHER INFORMATION: V domain of the light chain of humanized anti-
      6B4

<400> SEQUENCE: 10

Glu Asn Val Leu Thr Gln Ser Pro Ala Thr Leu Ser Leu Ser Pro Gly
1               5                  10                 15

Asp Arg Ala Thr Leu Ser Cys Arg Ala Thr Gln Ser Val Asn Arg Ser
                20                 25                 30

Leu Gly Trp Phe Gln Gln Lys Pro Gly Gln Ala Pro Arg Leu Leu Ile
                35                 40                 45

Tyr Asp Ser Phe Lys Arg Ala Ala Gly Val Pro Ala Arg Phe Ser Gly
                50                 55                 60

Ser Gly Ser Gly Thr Asp Phe Thr Leu Thr Ile Ser Thr Leu Glu Pro
65                 70                 75                 80

Glu Asp Phe Ala Val Tyr Tyr Cys Gln His Cys Arg Asn Trp Leu Val
```

-continued

```
                85                  90                  95

Thr Phe Gly Gln Gly Thr Arg Leu Glu Ile Lys
                100                 105

<210> SEQ ID NO 11
<211> LENGTH: 94
<212> TYPE: PRT
<213> ORGANISM: Artificial Sequence
<220> FEATURE:
<223> OTHER INFORMATION: V domain of the light chain of humanized anti-
      6B4

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp
                85                  90

<210> SEQ ID NO 12
<211> LENGTH: 90
<212> TYPE: PRT
<213> ORGANISM: Artificial Sequence
<220> FEATURE:
<223> OTHER INFORMATION: V domain of the light chain of humanized anti-
      6B4

<400> SEQUENCE: 12

Val Met Thr Gln Ser Pro Ala Phe Leu Ser Val Thr Pro Gly Glu Lys
1               5                   10                  15

Val Thr Ile Thr Cys Gln Ala Ser Glu Gly Ile Gly Asn Tyr Leu Tyr
            20                  25                  30

Trp Tyr Gln Gln Lys Pro Asp Gln Ala Pro Lys Leu Leu Ile Lys Tyr
        35                  40                  45

Ala Ser Gln Ser Ile Ser Gly Val Pro Ser Arg Phe Ser Gly Ser Gly
    50                  55                  60

Ser Gly Thr Asp Phe Thr Phe Thr Ile Ser Ser Leu Glu Ala Glu Asp
65                  70                  75                  80

Ala Ala Thr Tyr Tyr Cys Gln Gln Gly Asn
                85                  90

<210> SEQ ID NO 13
<211> LENGTH: 92
<212> TYPE: PRT
<213> ORGANISM: Artificial Sequence
<220> FEATURE:
<223> OTHER INFORMATION: V domain of the light chain of humanized anti-
      6B4

<400> SEQUENCE: 13

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30
```

```
Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
 50                  55                  60

Ser Gly Ser Gly Thr Asp Phe Thr Leu Thr Ile Asn Ser Leu Glu Ala
 65                  70                  75                  80

Glu Asp Ala Ala Thr Tyr Tyr Cys His Gln Ser Ser
                 85                  90
```

<210> SEQ ID NO 14
<211> LENGTH: 91
<212> TYPE: PRT
<213> ORGANISM: Artificial Sequence
<220> FEATURE:
<223> OTHER INFORMATION: V domain of the light chain of humanized anti-
      6B4

<400> SEQUENCE: 14

```
Leu Thr Gln Ser Pro Ser Phe Leu Ser Ala Ser Val Gly Asp Arg Val
 1               5                  10                  15

Thr Ile Thr Cys Arg Ala Ser Gln Gly Ile Ser Ser Tyr Leu Ala Trp
                 20                  25                  30

Tyr Gln Gln Lys Pro Gly Lys Ala Pro Lys Leu Leu Ile Tyr Ala Ala
        35                  40                  45

Ser Thr Leu Gln Ser Gly Val Pro Ser Arg Phe Ser Gly Ser Gly Ser
 50                  55                  60

Gly Thr Glu Phe Thr Leu Thr Ile Ser Ser Leu Gln Pro Glu Asp Phe
 65                  70                  75                  80

Ala Thr Tyr Tyr Cys Gln Gln Leu Asn Ser Tyr
                 85                  90
```

<210> SEQ ID NO 15
<211> LENGTH: 109
<212> TYPE: PRT
<213> ORGANISM: Artificial Sequence
<220> FEATURE:
<223> OTHER INFORMATION: V domain of the light chain of humanized anti-
      6B4

<400> SEQUENCE: 15

```
Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Pro Leu Thr Phe Gly Gln Gly Thr Lys Val Glu Ile Lys
                100                 105
```

<210> SEQ ID NO 16
<211> LENGTH: 103
<212> TYPE: PRT
<213> ORGANISM: Artificial Sequence

```
<220> FEATURE:
<223> OTHER INFORMATION: V domain of the light chain of humanized anti-
      6B4

<400> SEQUENCE: 16

Met Thr Gln Ser Pro Ser Thr Leu Ser Ala Ser Val Gly Asp Arg Val
1               5                   10                  15

Thr Ile Thr Cys Ser Ala Ser Ser Ile Ser Tyr Met His Trp Tyr
            20                  25                  30

Gln Gln Lys Pro Gly Lys Ala Pro Lys Leu Leu Ile Tyr Thr Thr Ser
        35                  40                  45

Asn Leu Ala Ser Gly Val Pro Ala Arg Phe Ser Gly Ser Gly Ser Gly
50                  55                  60

Thr Glu Phe Thr Leu Thr Ile Ser Ser Leu Gln Pro Asp Asp Phe Ala
65                  70                  75                  80

Thr Tyr Tyr Cys His Gln Arg Ser Thr Tyr Pro Leu Thr Phe Gly Gln
                85                  90                  95

Gly Thr Lys Val Glu Val Lys
            100

<210> SEQ ID NO 17
<211> LENGTH: 107
<212> TYPE: PRT
<213> ORGANISM: Artificial Sequence
<220> FEATURE:
<223> OTHER INFORMATION: V domain of the light chain of humanized anti-
      6B4

<400> SEQUENCE: 17

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln His Asn Glu Tyr Pro Tyr
                85                  90                  95

Thr Phe Gly Gln Gly Thr Lys Leu Glu Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: V domain of the light chain of humanized anti-
      6B4

<400> SEQUENCE: 18

Val Leu Thr Gln Ser Pro Ala Thr Leu Ser Leu Ser Pro Gly Glu Arg
1               5                   10                  15

Ala Thr Leu Ser Cys Arg Ala Ser Gln Ser Val Ser Ser Asn Tyr Leu
            20                  25                  30

Ala Trp Tyr Gln Gln Lys Pro Gly Gln Ala Pro Arg Leu Leu Ile Tyr
        35                  40                  45
```

```
Asp Ser Ser Arg Ala Thr Gly Val Pro Ala Arg Phe Ser Gly Ser
    50              55                  60

Gly Ser Gly Thr Asp Phe Thr Leu Thr Ile Ser Ser Leu Glu Pro Glu
 65              70                  75                  80

Asp Phe Ala Val Tyr Tyr Cys His Gln Tyr Ser Asp Ile Ser Pro Thr
                85                  90                  95

Phe Gly Gln Gly Thr Lys Val Glu Ile Lys
            100                 105

<210> SEQ ID NO 19
<211> LENGTH: 107
<212> TYPE: PRT
<213> ORGANISM: Artificial Sequence
<220> FEATURE:
<223> OTHER INFORMATION: V domain of the light chain of humanized anti-
      6B4

<400> SEQUENCE: 19

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
 65              70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: V domain of the light chain of humanized anti-
      6B4

<400> SEQUENCE: 20

Gln Thr Val Leu Thr Gln Ser Pro Ser Ser Leu Ser Val Ser Val Gly
 1               5                  10                  15

Asp Arg Val Thr Ile Thr Cys Arg Ala Ser Ser Ser Val Thr Tyr Ile
                20                  25                  30

His Trp Tyr Gln Gln Lys Pro Gly Leu Ala Pro Lys Ser Leu Ile Tyr
            35                  40                  45

Ala Thr Ser Asn Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
 65              70                  75                  80

Asp Ile Ala Thr Tyr Tyr Cys Gln His Trp Ser Ser Lys Pro Pro Thr
                85                  90                  95

Phe Gly Gln Gly Thr Lys Val Glu Val Lys
            100                 105

<210> SEQ ID NO 21
<211> LENGTH: 106
```

```
<212> TYPE: PRT
<213> ORGANISM: Artificial Sequence
<220> FEATURE:
<223> OTHER INFORMATION: 6B4-VL_humanized-2

<400> SEQUENCE: 21

Glu Asn Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Val
            20                  25                  30

His Trp Tyr Gln Gln Lys Pro Gly Gln Ala Pro Lys Leu Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Gln Gly Thr Lys Leu Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: 6B4-VL_humanized-3

<400> SEQUENCE: 22

Glu Asn Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Val
            20                  25                  30

His Trp Tyr Gln Gln Lys Pro Gly Gln Ala Pro Lys Leu Trp Ile Tyr
        35                  40                  45

Asp Thr Ser Lys Leu Ala Ser Gly Val Pro Ala Arg Phe Ser Gly Ser
    50                  55                  60

Gly Ser Gly Asn Asp Tyr Thr Leu Thr Ile Ser Ser Leu Glu Pro Glu
65                  70                  75                  80

Asp Phe Ala Val Tyr Tyr Cys Phe Gln Gly Ser Gly Tyr Pro Leu Thr
                85                  90                  95

Phe Gly Gln Gly Thr Lys Leu Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: 6B4-VL_humanized-4

<400> SEQUENCE: 23

Glu Asn Val Leu Thr Gln Ser Pro Ala Thr Leu Ser Leu Ser Pro Gly
1               5                   10                  15

Glu Arg Ala Thr Leu Ser Cys Ser Ala Arg Ser Ser Val Ser Tyr Val
            20                  25                  30

His Trp Tyr Gln Gln Lys Pro Gly Gln Ser Pro Lys Leu Trp Ile Tyr
        35                  40                  45

Asp Thr Ser Lys Leu Ala Ser Gly Val Pro Ala Arg Phe Ser Gly Ser
```

```
                50                  55                  60
Gly Ser Gly Asn Ser Tyr Thr Leu Thr Ile Ser Ser Leu Glu Pro Glu
 65                  70                  75                  80

Asp Phe Ala Val Tyr Tyr Cys Phe Gln Gly Ser Gly Tyr Pro Leu Thr
                 85                  90                  95

Phe Gly Gln Gly Thr Lys Leu Glu Ile Lys
                100                 105

<210> SEQ ID NO 24
<211> LENGTH: 112
<212> TYPE: PRT
<213> ORGANISM: Artificial Sequence
<220> FEATURE:
<223> OTHER INFORMATION: V domain of the heavy chain of mouse anti-6B4

<400> SEQUENCE: 24

Gln Val Gln Leu Gln Gln Pro Gly Ser Glu Leu Val Arg Pro Gly Ala
 1               5                  10                  15

Ser Val Lys Leu Ser Cys Lys Ala Ser Gly Tyr Thr Phe Thr Thr Tyr
                 20                  25                  30

Trp Ile His Trp Val Arg Gln Arg Pro Gly Gln Gly Leu Glu Trp Ile
             35                  40                  45

Gly Asn Ile Tyr Pro Gly Gly Asp Ser Ser Asn Tyr Asp Glu Lys Val
 50                  55                  60

Lys Ser Arg Ala Thr Leu Thr Val Asp Thr Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ser Arg Trp Gly Ile Trp Gly Gln Gly Thr Leu Val Thr Val Ser Ala
                100                 105                 110

<210> SEQ ID NO 25
<211> LENGTH: 112
<212> TYPE: PRT
<213> ORGANISM: Artificial Sequence
<220> FEATURE:
<223> OTHER INFORMATION: 6B4-VH_humanized-1

<400> SEQUENCE: 25

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Thr Tyr
                 20                  25                  30

Trp Ile His Trp Val Arg Gln Ala Pro Gly Gln Gly Leu Glu Trp Met
             35                  40                  45

Gly Asn Ile Tyr Pro Gly Gly Asp Ser Ser Asn Tyr Asp Glu Lys Val
 50                  55                  60

Lys Ser Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ser Arg Trp Gly Ile Trp Gly Gln Gly Thr Leu Val Thr Val Ser Ser
                100                 105                 110

<210> SEQ ID NO 26
<211> LENGTH: 129
<212> TYPE: PRT
<213> ORGANISM: Artificial Sequence
<220> FEATURE:
```

<223> OTHER INFORMATION: V domain of the heavy chain of humanized anti-
      6B4
<220> FEATURE:
<221> NAME/KEY: VARIANT
<222> LOCATION: 115
<223> OTHER INFORMATION: Xaa = Any Amino Acid

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Asn Pro Tyr Gly Asn Gly Asp Thr Asn Tyr Ala Gln Lys
50                  55                  60

Phe Gln Gly Arg Val Thr Ile Thr Ala Asp Thr Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Pro Gly Tyr Gly Ser Gly Gly Cys Tyr Arg Gly
            100                 105                 110

Asp Tyr Xaa Phe Asp Tyr Trp Gly Gln Gly Thr Leu Val Thr Val Ser
        115                 120                 125

Ser

<210> SEQ ID NO 27
<211> LENGTH: 115
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 27

Glu Val Gln Leu Val Gln Ser Gly Gly Glu Val Arg Lys Pro Gly Ala
1               5                   10                  15

Ser Val Lys Val Ser Cys Lys Ala Ser Gly Tyr Thr Phe Thr Asn Tyr
            20                  25                  30

Tyr Leu His Trp Val Arg Gln Ala Pro Gly Gln Gly Leu Glu Trp Val
        35                  40                  45

Gly Val Ile Asn Pro Arg Gly Gly Ala Thr Ser His Ala Gln Lys Phe
50                  55                  60

Gln Gly Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Leu Phe Gln His Trp Gly Gln Gly Thr Leu Val Thr
            100                 105                 110

Val Ser Ser
        115

<210> SEQ ID NO 28
<211> LENGTH: 118
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 28

Glu Val Gln Leu Val Gln Ser Gly Ala Glu Met Lys Lys Pro Gly Ala
1               5                   10                  15

Ser Val Lys Val Ser Cys Lys Ala Ser Gly Tyr Ser Phe Ser Ile Tyr
            20                  25                  30

Asn Ile His Trp Val Arg Gln Ala Pro Gly Gln Gly Leu Glu Trp Met
        35                  40                  45

Gly Trp Ile His Ala Gly Thr Gly Asn Arg Lys Tyr Ser Gln Val Phe
    50                  55                  60

Gln Asp Arg Val Thr Ile Thr Arg Asp Thr Ser Ala Ser Thr Ser Tyr
65                  70                  75                  80

Met Glu Leu Ser Ser Leu Thr Ser Glu Asp Thr Ala Val Tyr Tyr Cys
                85                  90                  95

Ala Arg Asp Pro Asn Phe Gly Asp Phe Asp Ser Trp Gly Gln Gly Thr
            100                 105                 110

Leu Val Thr Val Ser Ser
            115

<210> SEQ ID NO 29
<211> LENGTH: 115
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 29

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Ala Ala Val Ala Gly Trp Gly Gln Gly Thr Leu Val Thr
            100                 105                 110

Val Ser Ser
        115

<210> SEQ ID NO 30
<211> LENGTH: 118
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 30

Glu Val Gln Leu Leu Glu Ser Gly Ala Glu Ala Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val His Gln Ala Pro Gly Gln Arg Leu Glu Trp Met

```
            35                  40                  45

Gly Glu Ile Asn Pro Gly Asn Gly His Thr Asn Tyr Asn Glu Lys Phe
        50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Glu Gly Glu Trp Gly Ser Phe Glu Tyr Trp Gly Gln Gly Thr
            100                 105                 110

Leu Val Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ile Thr His Asp Ala Phe Asp Ile Trp Gly Gln Gly Thr Met Val
            100                 105                 110

Thr Val Ser Ser
        115

<210> SEQ ID NO 32
<211> LENGTH: 98
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                    85                  90                  95

Ala Arg

<210> SEQ ID NO 33
<211> LENGTH: 98
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Ser Asn Gly Asn Thr Asn Tyr Ala Gln Lys Leu
        50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 34
<211> LENGTH: 98
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 35
<211> LENGTH: 129
<212> TYPE: PRT
<213> ORGANISM: Artificial Sequence
<220> FEATURE:
<223> OTHER INFORMATION: V domain of the heavy chain of humanized anti-
      6B4
<220> FEATURE:
<221> NAME/KEY: VARIANT
<222> LOCATION: 115
<223> OTHER INFORMATION: Xaa = Any Amino Acid
```

```
<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
        35                  40                  45

Gly Trp Ile Asn Pro Tyr Gly Asn Gly Asp Thr Asn Tyr Ala Gln Lys
    50                  55                  60

Phe Gln Gly Arg Val Thr Ile Thr Ala Asp Thr Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Arg Ala Pro Gly Tyr Gly Ser Gly Gly Cys Tyr Arg Gly
            100                 105                 110

Asp Tyr Xaa Phe Asp Tyr Trp Gly Gln Gly Thr Leu Val Thr Val Ser
        115                 120                 125

Ser

<210> SEQ ID NO 36
<211> LENGTH: 118
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 36

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Ile Phe Thr Ser Tyr
            20                  25                  30

Tyr Met Tyr Trp Val Lys Gln Ala Pro Gly Gln Gly Leu Glu Trp Ile
        35                  40                  45

Gly Glu Ile Asn Pro Ser Asn Gly Asp Thr Asn Phe Asn Glu Lys Phe
    50                  55                  60

Lys Ser Lys Ala Thr Leu Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ser Asp Gly Arg Asn Asp Met Asp Ser Trp Gly Gln Gly Thr
            100                 105                 110

Leu Val Thr Val Ser Ser
        115

<210> SEQ ID NO 37
<211> LENGTH: 116
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 37

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30
```

```
Arg Met His Trp Val Arg Gln Ala Pro Gly Gln Gly Leu Glu Trp Ile
        35                  40                  45

Gly Tyr Ile Asn Pro Ser Thr Gly Tyr Thr Glu Tyr Asn Gln Lys Phe
    50                  55                  60

Lys Asp Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Val Tyr Tyr Cys
                85                  90                  95

Ala Arg Gly Gly Gly Val Phe Asp Tyr Trp Gly Gln Gly Thr Leu Val
            100                 105                 110

Thr Val Ser Ser
        115

<210> SEQ ID NO 38
<211> LENGTH: 117
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 38

Gln Val Gln Leu Leu Glu Ser Gly Ala Val Leu Ala Arg Pro Gly Thr
 1               5                  10                  15

Ser Val Lys Ile Ser Cys Lys Ala Ser Gly Phe Asn Ile Lys Asp Tyr
                20                  25                  30

Tyr Met His Trp Val Lys Gln Arg Pro Gly Gln Gly Leu Glu Trp Ile
        35                  40                  45

Gly Gly Asn Asp Pro Ala Asn Gly His Ser Met Tyr Asp Pro Lys Phe
    50                  55                  60

Gln Gly Arg Val Thr Ile Thr Ala Asp Thr Ser Ser Thr Val Phe
 65                  70                  75                  80

Met Glu Leu Ser Ser Leu Arg Ser Glu Asp Thr Ala Val Tyr Tyr Cys
                85                  90                  95

Ala Arg Asp Ser Gly Tyr Ala Met Asp Tyr Trp Gly Gln Gly Thr Leu
            100                 105                 110

Val Thr Val Ser Ser
        115

<210> SEQ ID NO 39
<211> LENGTH: 123
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 39

Gln Val Gln Leu Gln Gln Ser Gly Ala Glu Val Lys Lys Pro Gly Ser
 1               5                  10                  15

Ser Val Lys Val Ser Cys Lys Ala Ser Gly Tyr Thr Phe Thr Asn Tyr
                20                  25                  30

Tyr Ile Tyr Trp Val Arg Gln Ala Pro Gly Gln Gly Leu Glu Trp Ile
        35                  40                  45

Gly Gly Ile Asn Pro Thr Ser Gly Gly Ser Asn Phe Asn Glu Lys Phe
    50                  55                  60

Lys Thr Arg Val Thr Ile Thr Ala Asp Glu Ser Ser Thr Thr Ala Tyr
 65                  70                  75                  80
```

```
Met Glu Leu Ser Ser Leu Arg Ser Glu Asp Thr Ala Phe Tyr Phe Cys
                85                  90                  95

Thr Arg Gln Gly Leu Trp Phe Asp Ser Asp Gly Arg Gly Phe Asp Phe
            100                 105                 110

Trp Gly Gln Gly Thr Thr Val Thr Val Ser Ser
        115                 120

<210> SEQ ID NO 40
<211> LENGTH: 118
<212> TYPE: PRT
<213> ORGANISM: Artificial Sequence
<220> FEATURE:
<223> OTHER INFORMATION: V domain of the heavy chain of humanized anti-
      6B4

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Asn Ile Tyr Pro Gly Ser Gly Thr Asn Tyr Ala Glu Lys Phe
    50                  55                  60

Lys Asn Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Gly Pro Tyr Phe Phe Asp Tyr Trp Gly Gln Gly Thr
            100                 105                 110

Leu Val Thr Val Ser Ser
        115

<210> SEQ ID NO 41
<211> LENGTH: 112
<212> TYPE: PRT
<213> ORGANISM: Artificial Sequence
<220> FEATURE:
<223> OTHER INFORMATION: 6B4-VH_humanized-2

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Trp Ile His Trp Val Arg Gln Ala Pro Gly Gln Gly Leu Glu Trp Ile
        35                  40                  45

Gly Asn Ile Tyr Pro Gly Gly Asp Ser Ser Asn Tyr Asp Glu Lys Val
    50                  55                  60

Lys Ser Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Gly Ile Trp Gly Gln Gly Thr Leu Val Thr Val Ser Ser
            100                 105                 110

<210> SEQ ID NO 42
<211> LENGTH: 233
```

```
<212> TYPE: PRT
<213> ORGANISM: Artificial Sequence
<220> FEATURE:
<223> OTHER INFORMATION: 6B4 Light (Kappa) Chain Humanized Variant 1

<400> SEQUENCE: 42

Met Val Leu Gln Thr Gln Val Phe Ile Ser Leu Leu Leu Trp Ile Ser
1               5                   10                  15

Gly Ala Tyr Gly Glu Asn Val Leu Thr Gln Ser Pro Ala Thr Leu Ser
                20                  25                  30

Leu Ser Pro Gly Glu Arg Ala Thr Leu Ser Cys Ser Ala Arg Ser Ser
            35                  40                  45

Val Ser Tyr Val His Trp Tyr Gln Gln Lys Pro Gly Gln Ala Pro Arg
    50                  55                  60

Leu Leu Ile Tyr Asp Thr Ser Lys Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Phe Gln Gly Ser Gly
            100                 105                 110

Tyr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 43
<211> LENGTH: 233
<212> TYPE: PRT
<213> ORGANISM: Artificial Sequence
<220> FEATURE:
<223> OTHER INFORMATION: 6B4 Light (Kappa) Chain Humanized Variant 2

<400> SEQUENCE: 43

Met Val Leu Gln Thr Gln Val Phe Ile Ser Leu Leu Leu Trp Ile Ser
1               5                   10                  15

Gly Ala Tyr Gly Glu Asn Val Leu Thr Gln Ser Pro Ala Thr Leu Ser
                20                  25                  30

Leu Ser Pro Gly Glu Arg Ala Thr Leu Ser Cys Ser Ala Arg Ser Ser
            35                  40                  45

Val Ser Tyr Val His Trp Tyr Gln Gln Lys Pro Gly Gln Ala Pro Lys
    50                  55                  60

Leu Trp Ile Tyr Asp Thr Ser Lys Leu Ala Ser Gly Val Pro Ala Arg
65                  70                  75                  80

Phe Ser Gly Ser Gly Ser Gly Thr Asp Phe Thr Leu Thr Ile Ser Ser
                85                  90                  95
```

Leu Glu Pro Glu Asp Phe Ala Val Tyr Tyr Cys Phe Gln Gly Ser Gly
            100                 105                 110

Tyr Pro Leu Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
        180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 44
<211> LENGTH: 233
<212> TYPE: PRT
<213> ORGANISM: Artificial Sequence
<220> FEATURE:
<223> OTHER INFORMATION: 6B4 Light (Kappa) Chain Humanized Variant 3

<400> SEQUENCE: 44

Met Val Leu Gln Thr Gln Val Phe Ile Ser Leu Leu Leu Trp Ile Ser
1               5                   10                  15

Gly Ala Tyr Gly Glu Asn Val Leu Thr Gln Ser Pro Ala Thr Leu Ser
            20                  25                  30

Leu Ser Pro Gly Glu Arg Ala Thr Leu Ser Cys Ser Ala Arg Ser Ser
        35                  40                  45

Val Ser Tyr Val His Trp Tyr Gln Gln Lys Pro Gly Gln Ala Pro Lys
50                  55                  60

Leu Trp Ile Tyr Asp Thr Ser Lys Leu Ala Ser Gly Val Pro Ala Arg
65                  70                  75                  80

Phe Ser Gly Ser Gly Ser Gly Asn Asp Tyr Thr Leu Thr Ile Ser Ser
            85                  90                  95

Leu Glu Pro Glu Asp Phe Ala Val Tyr Tyr Cys Phe Gln Gly Ser Gly
            100                 105                 110

Tyr Pro Leu Thr Phe Gly Gln Gly Thr Lys Leu Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
            165                 170                 175

Asn Ser Gln Glu Ser Val Thr Glu Gln Asp Ser Lys Asp Ser Thr Tyr
        180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

```
Thr Lys Ser Phe Asn Arg Gly Glu Cys
225                 230

<210> SEQ ID NO 45
<211> LENGTH: 233
<212> TYPE: PRT
<213> ORGANISM: Artificial Sequence
<220> FEATURE:
<223> OTHER INFORMATION: 6B4 Light (Kappa) Chain Humanized Variant 4

<400> SEQUENCE: 45

Met Val Leu Gln Thr Gln Val Phe Ile Ser Leu Leu Trp Ile Ser
1               5                   10                  15

Gly Ala Tyr Gly Glu Asn Val Leu Thr Gln Ser Pro Ala Thr Leu Ser
                20                  25                  30

Leu Ser Pro Gly Glu Arg Ala Thr Leu Ser Cys Ser Ala Arg Ser Ser
            35                  40                  45

Val Ser Tyr Val His Trp Tyr Gln Gln Lys Pro Gly Gln Ser Pro Lys
    50                  55                  60

Leu Trp Ile Tyr Asp Thr Ser Lys Leu Ala Ser Gly Val Pro Ala Arg
65                  70                  75                  80

Phe Ser Gly Ser Gly Ser Gly Asn Ser Tyr Thr Leu Thr Ile Ser Ser
                85                  90                  95

Leu Glu Pro Glu Asp Phe Ala Val Tyr Tyr Cys Phe Gln Gly Ser Gly
            100                 105                 110

Tyr Pro Leu Thr Phe Gly Gln Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 46
<211> LENGTH: 458
<212> TYPE: PRT
<213> ORGANISM: Artificial Sequence
<220> FEATURE:
<223> OTHER INFORMATION: 6B4 Heavy (Igg4) Chain Humanized Variant 1

<400> SEQUENCE: 46

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Thr Tyr Trp Ile His Trp Val Arg Gln Ala Pro Gly Gln Gly Leu
```

```
        50                  55                  60
Glu Trp Met Gly Asn Ile Tyr Pro Gly Gly Asp Ser Ser Asn Tyr Asp
 65                  70                  75                  80

Glu Lys Val Lys Ser Arg Val Thr Ile Thr Ala Asp Thr Ser Thr Ser
                 85                  90                  95

Thr Ala Tyr Met Glu Leu Ser Ser Leu Arg Ser Glu Asp Thr Ala Val
            100                 105                 110

Tyr Tyr Cys Ser Arg Trp Gly Ile Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Lys Thr Tyr Thr Cys Asn Val Asp His Lys Pro Ser Asn Thr Lys
    210                 215                 220

Val Asp Lys Arg Val Glu Ser Lys Tyr Gly Pro Pro Cys Pro Ser Cys
225                 230                 235                 240

Pro Ala Pro Glu Phe Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Glu Asp Pro Glu Val Gln Phe Asn Trp
        275                 280                 285

Tyr Val Asp Gly Val Glu Val His Asn Ala Lys Thr Lys Pro Arg Glu
    290                 295                 300

Glu Gln Phe Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Gly Leu Pro Ser Ser Ile Glu Lys Thr Ile Ser Lys Ala Lys Gly
            340                 345                 350

Gln Pro Arg Glu Pro Gln Val Tyr Thr Leu Pro Pro Ser Gln Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Arg Leu Thr Val Asp Lys Ser Arg Trp Gln Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Leu Gly Lys
    450                 455

<210> SEQ ID NO 47
```

<211> LENGTH: 458
<212> TYPE: PRT
<213> ORGANISM: Artificial Sequence
<220> FEATURE:
<223> OTHER INFORMATION: 6B4 Heavy (Igg4) Chain Humanized Variant 2

<400> SEQUENCE: 47

Met Asp Trp Thr Trp Arg Ile Leu Phe Leu Val Ala Ala Ala Thr Gly
1               5                   10                  15

Thr His Ala Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Tyr Trp Ile His Trp Val Arg Gln Ala Pro Gly Gln Gly Leu
    50                  55                  60

Glu Trp Ile Gly Asn Ile Tyr Pro Gly Gly Asp Ser Ser Asn Tyr Asp
65                  70                  75                  80

Glu Lys Val Lys Ser Arg Ala Thr Leu Thr Val Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ser Arg Trp Gly Ile Trp Gly Gln Gly Thr Leu Val Thr
        115                 120                 125

Val Ser Ser Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Lys Thr Tyr Thr Cys Asn Val Asp His Lys Pro Ser Asn Thr Lys
    210                 215                 220

Val Asp Lys Arg Val Glu Ser Lys Tyr Gly Pro Pro Cys Pro Ser Cys
225                 230                 235                 240

Pro Ala Pro Glu Phe Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Glu Asp Pro Glu Val Gln Phe Asn Trp
        275                 280                 285

Tyr Val Asp Gly Val Glu Val His Asn Ala Lys Thr Lys Pro Arg Glu
    290                 295                 300

Glu Gln Phe Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Gly Leu Pro Ser Ser Ile Glu Lys Thr Ile Ser Lys Ala Lys Gly
            340                 345                 350

Gln Pro Arg Glu Pro Gln Val Tyr Thr Leu Pro Pro Ser Gln Glu Glu
        355                 360                 365

Met Thr Lys Asn Gln Val Ser Leu Thr Cys Leu Val Lys Gly Phe Tyr
    370                 375                 380

```
Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Arg Leu Thr Val Asp Lys Ser Arg Trp Gln Glu Gly Asn
        420                 425                 430

Val Phe Ser Cys Ser Val Met His Glu Ala Leu His Asn His Tyr Thr
    435                 440                 445

Gln Lys Ser Leu Ser Leu Ser Leu Gly Lys
    450                 455

<210> SEQ ID NO 48
<211> LENGTH: 458
<212> TYPE: PRT
<213> ORGANISM: Artificial Sequence
<220> FEATURE:
<223> OTHER INFORMATION: 6B4 Heavy (Igg4) Chain Chimeric

<400> SEQUENCE: 48

Met Asp Trp Thr Trp Arg Ile Leu Phe Leu Val Ala Ala Ala Thr Gly
1               5                   10                  15

Thr His Ala Gln Val Gln Leu Gln Gln Pro Gly Ser Glu Leu Val Arg
            20                  25                  30

Pro Gly Ala Ser Val Lys Leu Ser Cys Lys Ala Ser Gly Tyr Thr Phe
        35                  40                  45

Thr Thr Tyr Trp Ile His Trp Val Arg Gln Arg Pro Gly Gln Gly Leu
    50                  55                  60

Glu Trp Ile Gly Asn Ile Tyr Pro Gly Gly Asp Ser Ser Asn Tyr Asp
65                  70                  75                  80

Glu Lys Val Lys Ser Arg Ala Thr Leu Thr Val Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ser Arg Trp Gly Ile Trp Gly Gln Gly Thr Leu Val Thr
        115                 120                 125

Val Ser Ala Ala Ser Thr Lys Gly Pro Ser Val Phe Pro Leu Ala Pro
    130                 135                 140

Cys Ser Arg Ser Thr Ser Glu Ser Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Lys Thr Tyr Thr Cys Asn Val Asp His Lys Pro Ser Asn Thr Lys
    210                 215                 220

Val Asp Lys Arg Val Glu Ser Lys Tyr Gly Pro Pro Cys Pro Ser Cys
225                 230                 235                 240

Pro Ala Pro Glu Phe Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Glu Asp Pro Glu Val Gln Phe Asn Trp
        275                 280                 285
```

```
Tyr Val Asp Gly Val Glu Val His Asn Ala Lys Thr Lys Pro Arg Glu
            290                 295                 300

Glu Gln Phe Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
            325                 330                 335

Lys Gly Leu Pro Ser Ser Ile Glu Lys Thr Ile Ser Lys Ala Lys Gly
            340                 345                 350

Gln Pro Arg Glu Pro Gln Val Tyr Thr Leu Pro Pro Ser Gln Glu Glu
            355                 360                 365

Met Thr Lys Asn Gln Val Ser Leu Thr Cys Leu Val Lys Gly Phe Tyr
            370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
            405                 410                 415

Leu Tyr Ser Arg Leu Thr Val Asp Lys Ser Arg Trp Gln Glu Gly Asn
            420                 425                 430

Val Phe Ser Cys Ser Val Met His Glu Ala Leu His Asn His Tyr Thr
            435                 440                 445

Gln Lys Ser Leu Ser Leu Ser Leu Gly Lys
       450                 455

<210> SEQ ID NO 49
<211> LENGTH: 12
<212> TYPE: PRT
<213> ORGANISM: Artificial Sequence
<220> FEATURE:
<223> OTHER INFORMATION: S100A9 N-term

<400> SEQUENCE: 49

Met Thr Cys Lys Met Ser Gln Leu Glu Arg Asn Ile
1               5                   10

<210> SEQ ID NO 50
<211> LENGTH: 14
<212> TYPE: PRT
<213> ORGANISM: Artificial Sequence
<220> FEATURE:
<223> OTHER INFORMATION: S100A9 Hinge

<400> SEQUENCE: 50

Asp Leu Gln Asn Phe Leu Lys Lys Glu Asn Lys Asn Glu Lys
1               5                   10

<210> SEQ ID NO 51
<211> LENGTH: 28
<212> TYPE: PRT
<213> ORGANISM: Artificial Sequence
<220> FEATURE:
<223> OTHER INFORMATION: S100A9 C-term

<400> SEQUENCE: 51

Thr Trp Ala Ser His Glu Lys Met His Glu Gly Asp Glu Gly Pro Gly
1               5                   10                  15

His His His Lys Pro Gly Leu Gly Glu Gly Thr Pro
            20                  25

<210> SEQ ID NO 52
<211> LENGTH: 28
```

```
<212> TYPE: PRT
<213> ORGANISM: Artificial Sequence
<220> FEATURE:
<223> OTHER INFORMATION: S100A9 C-term

<400> SEQUENCE: 52

Thr Trp Ala Ser His Glu Lys Met His Glu Gly Asp Glu Gly Pro Gly
1               5                   10                  15
His His His Lys Pro Gly Leu Gly Glu Gly Thr Pro
            20                  25

<210> SEQ ID NO 53
<211> LENGTH: 9
<212> TYPE: PRT
<213> ORGANISM: Artificial Sequence
<220> FEATURE:
<223> OTHER INFORMATION: S100A9 C1

<400> SEQUENCE: 53

Thr Trp Ala Ser His Glu Lys Met His
1               5

<210> SEQ ID NO 54
<211> LENGTH: 9
<212> TYPE: PRT
<213> ORGANISM: Artificial Sequence
<220> FEATURE:
<223> OTHER INFORMATION: S100A9 C2

<400> SEQUENCE: 54

Ser His Glu Lys Met His Glu Gly Asp
1               5

<210> SEQ ID NO 55
<211> LENGTH: 9
<212> TYPE: PRT
<213> ORGANISM: Artificial Sequence
<220> FEATURE:
<223> OTHER INFORMATION: S100A9 C3

<400> SEQUENCE: 55

Lys Met His Glu Gly Asp Glu Gly Pro
1               5

<210> SEQ ID NO 56
<211> LENGTH: 9
<212> TYPE: PRT
<213> ORGANISM: Artificial Sequence
<220> FEATURE:
<223> OTHER INFORMATION: S100A9 C4

<400> SEQUENCE: 56

Glu Gly Asp Glu Gly Pro Gly His His
1               5

<210> SEQ ID NO 57
<211> LENGTH: 9
<212> TYPE: PRT
<213> ORGANISM: Artificial Sequence
<220> FEATURE:
<223> OTHER INFORMATION: S100A9 C5

<400> SEQUENCE: 57

Glu Gly Pro Gly His His His Lys Pro
1               5
```

```
<210> SEQ ID NO 58
<211> LENGTH: 9
<212> TYPE: PRT
<213> ORGANISM: Artificial Sequence
<220> FEATURE:
<223> OTHER INFORMATION: S100A9 C6

<400> SEQUENCE: 58

Gly His His His Lys Pro Gly Leu Gly
1               5

<210> SEQ ID NO 59
<211> LENGTH: 10
<212> TYPE: PRT
<213> ORGANISM: Artificial Sequence
<220> FEATURE:
<223> OTHER INFORMATION: S100A9 C7

<400> SEQUENCE: 59

His Lys Pro Gly Leu Gly Glu Gly Thr Pro
1               5                   10

<210> SEQ ID NO 60
<211> LENGTH: 8
<212> TYPE: PRT
<213> ORGANISM: Artificial Sequence
<220> FEATURE:
<223> OTHER INFORMATION: S100A9 C6a

<400> SEQUENCE: 60

Gly Pro Gly His His His Lys Pro
1               5

<210> SEQ ID NO 61
<211> LENGTH: 8
<212> TYPE: PRT
<213> ORGANISM: Artificial Sequence
<220> FEATURE:
<223> OTHER INFORMATION: S100A9 C6b

<400> SEQUENCE: 61

Pro Gly His His His Lys Pro Gly
1               5

<210> SEQ ID NO 62
<211> LENGTH: 8
<212> TYPE: PRT
<213> ORGANISM: Artificial Sequence
<220> FEATURE:
<223> OTHER INFORMATION: S100A9 C6c

<400> SEQUENCE: 62

Gly His His His Lys Pro Gly Leu
1               5

<210> SEQ ID NO 63
<211> LENGTH: 8
<212> TYPE: PRT
<213> ORGANISM: Artificial Sequence
<220> FEATURE:
<223> OTHER INFORMATION: S100A9 C6d

<400> SEQUENCE: 63

His His His Lys Pro Gly Leu Gly
1               5

<210> SEQ ID NO 64
```

```
<211> LENGTH: 8
<212> TYPE: PRT
<213> ORGANISM: Artificial Sequence
<220> FEATURE:
<223> OTHER INFORMATION: S100A9 C6e

<400> SEQUENCE: 64

His His Lys Pro Gly Leu Gly Glu
1               5

<210> SEQ ID NO 65
<211> LENGTH: 8
<212> TYPE: PRT
<213> ORGANISM: Artificial Sequence
<220> FEATURE:
<223> OTHER INFORMATION: S100A9 C6f

<400> SEQUENCE: 65

His Lys Pro Gly Leu Gly Glu Gly
1               5

<210> SEQ ID NO 66
<211> LENGTH: 8
<212> TYPE: PRT
<213> ORGANISM: Artificial Sequence
<220> FEATURE:
<223> OTHER INFORMATION: S100A9 C6g

<400> SEQUENCE: 66

Lys Pro Gly Leu Gly Glu Gly Thr
1               5

<210> SEQ ID NO 67
<211> LENGTH: 8
<212> TYPE: PRT
<213> ORGANISM: Artificial Sequence
<220> FEATURE:
<223> OTHER INFORMATION: S100A9 C7a

<400> SEQUENCE: 67

Pro Gly Leu Gly Glu Gly Thr Pro
1               5

<210> SEQ ID NO 68
<211> LENGTH: 6
<212> TYPE: PRT
<213> ORGANISM: Artificial Sequence
<220> FEATURE:
<223> OTHER INFORMATION: S100A9 C7b

<400> SEQUENCE: 68

Leu Gly Glu Gly Thr Pro
1               5

<210> SEQ ID NO 69
<211> LENGTH: 4
<212> TYPE: PRT
<213> ORGANISM: Artificial Sequence
<220> FEATURE:
<223> OTHER INFORMATION: S100A9 C7c

<400> SEQUENCE: 69

Glu Gly Thr Pro
1

<210> SEQ ID NO 70
<211> LENGTH: 6
```

```
<212> TYPE: PRT
<213> ORGANISM: Artificial Sequence
<220> FEATURE:
<223> OTHER INFORMATION: epitope recognized by humanized 6B4 antibody
<220> FEATURE:
<221> NAME/KEY: VARIANT
<222> LOCATION: 3, 4, 6
<223> OTHER INFORMATION: Xaa = Any Amino Acid

<400> SEQUENCE: 70

Leu Gly Xaa Xaa Thr Xaa
1               5

<210> SEQ ID NO 71
<211> LENGTH: 6
<212> TYPE: PRT
<213> ORGANISM: Artificial Sequence
<220> FEATURE:
<223> OTHER INFORMATION: epitope recognized by humanized 6B4 antibody
<220> FEATURE:
<221> NAME/KEY: VARIANT
<222> LOCATION: 4
<223> OTHER INFORMATION: Xaa = Any Amino Acid

<400> SEQUENCE: 71

Leu Gly Glu Xaa Thr Pro
1               5

<210> SEQ ID NO 72
<211> LENGTH: 8
<212> TYPE: PRT
<213> ORGANISM: Artificial Sequence
<220> FEATURE:
<223> OTHER INFORMATION: epitope recognized by humanized 6B4 antibody
<220> FEATURE:
<221> NAME/KEY: VARIANT
<222> LOCATION: 6
<223> OTHER INFORMATION: Xaa = Any Amino Acid

<400> SEQUENCE: 72

Pro Gly Leu Gly Glu Xaa Thr Pro
1               5

<210> SEQ ID NO 73
<211> LENGTH: 113
<212> TYPE: PRT
<213> ORGANISM: Artificial Sequence
<220> FEATURE:
<223> OTHER INFORMATION: mouse S100A9

<400> SEQUENCE: 73

Met Ala Asn Lys Ala Pro Ser Gln Met Glu Arg Ser Ile Thr Thr Ile
1               5                   10                  15

Ile Asp Thr Phe His Gln Tyr Ser Arg Lys Glu Gly His Pro Asp Thr
            20                  25                  30

Leu Ser Lys Lys Glu Phe Arg Gln Met Val Glu Ala Gln Leu Ala Thr
        35                  40                  45

Phe Met Lys Lys Glu Lys Arg Asn Glu Ala Leu Ile Asn Asp Ile Met
    50                  55                  60

Glu Asp Leu Asp Thr Asn Gln Asp Asn Gln Leu Ser Phe Glu Glu Cys
65                  70                  75                  80

Met Met Leu Met Ala Lys Leu Ile Phe Ala Cys His Glu Lys Leu His
                85                  90                  95

Glu Asn Asn Pro Arg Gly His Gly His Ser His Gly Lys Gly Cys Gly
            100                 105                 110
```

Lys

<210> SEQ ID NO 74
<211> LENGTH: 114
<212> TYPE: PRT
<213> ORGANISM: Artificial Sequence
<220> FEATURE:
<223> OTHER INFORMATION: human S100A9

<400> SEQUENCE: 74

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro
```

<210> SEQ ID NO 75
<211> LENGTH: 784
<212> TYPE: PRT
<213> ORGANISM: Artificial Sequence
<220> FEATURE:
<223> OTHER INFORMATION: mouse TLR2

<400> SEQUENCE: 75

```
Met Leu Arg Ala Leu Trp Leu Phe Trp Ile Leu Val Ala Ile Thr Val
1               5                   10                  15

Leu Phe Ser Lys Arg Cys Ser Ala Gln Glu Ser Leu Ser Cys Asp Ala
            20                  25                  30

Ser Gly Val Cys Asp Gly Arg Ser Arg Ser Phe Thr Ser Ile Pro Ser
        35                  40                  45

Gly Leu Thr Ala Ala Met Lys Ser Leu Asp Leu Ser Phe Asn Lys Ile
    50                  55                  60

Thr Tyr Ile Gly His Gly Asp Leu Arg Ala Cys Ala Asn Leu Gln Val
65                  70                  75                  80

Leu Met Leu Lys Ser Ser Arg Ile Asn Thr Ile Glu Gly Asp Ala Phe
                85                  90                  95

Tyr Ser Leu Gly Ser Leu Glu His Leu Asp Leu Ser Asp Asn His Leu
            100                 105                 110

Ser Ser Leu Ser Ser Ser Trp Phe Gly Pro Leu Ser Ser Leu Lys Tyr
        115                 120                 125

Leu Asn Leu Met Gly Asn Pro Tyr Gln Thr Leu Gly Val Thr Ser Leu
    130                 135                 140

Phe Pro Asn Leu Thr Asn Leu Gln Thr Leu Arg Ile Gly Asn Val Glu
145                 150                 155                 160

Thr Phe Ser Glu Ile Arg Arg Ile Asp Phe Ala Gly Leu Thr Ser Leu
                165                 170                 175

Asn Glu Leu Glu Ile Lys Ala Leu Ser Leu Arg Asn Tyr Gln Ser Gln
```

```
              180                 185                 190
Ser Leu Lys Ser Ile Arg Asp Ile His His Leu Thr Leu His Leu Ser
            195                 200                 205
Glu Ser Ala Phe Leu Leu Glu Ile Phe Ala Asp Ile Leu Ser Ser Val
            210                 215                 220
Arg Tyr Leu Glu Leu Arg Asp Thr Asn Leu Ala Arg Phe Gln Phe Ser
225                 230                 235                 240
Pro Leu Pro Val Asp Glu Val Ser Ser Pro Met Lys Lys Leu Ala Phe
                245                 250                 255
Arg Gly Ser Val Leu Thr Asp Glu Ser Phe Asn Glu Leu Leu Lys Leu
            260                 265                 270
Leu Arg Tyr Ile Leu Glu Leu Ser Glu Val Glu Phe Asp Asp Cys Thr
            275                 280                 285
Leu Asn Gly Leu Gly Asp Phe Asn Pro Ser Glu Ser Asp Val Val Ser
            290                 295                 300
Glu Leu Gly Lys Val Glu Thr Val Thr Ile Arg Arg Leu His Ile Pro
305                 310                 315                 320
Gln Phe Tyr Leu Phe Tyr Asp Leu Ser Thr Val Tyr Ser Leu Leu Glu
                325                 330                 335
Lys Val Lys Arg Ile Thr Val Glu Asn Ser Lys Val Phe Leu Val Pro
            340                 345                 350
Cys Ser Phe Ser Gln His Leu Lys Ser Leu Glu Phe Leu Asp Leu Ser
            355                 360                 365
Glu Asn Leu Met Val Glu Glu Tyr Leu Lys Asn Ser Ala Cys Lys Gly
            370                 375                 380
Ala Trp Pro Ser Leu Gln Thr Leu Val Leu Ser Gln Asn His Leu Arg
385                 390                 395                 400
Ser Met Gln Lys Thr Gly Glu Ile Leu Leu Thr Leu Lys Asn Leu Thr
                405                 410                 415
Ser Leu Asp Ile Ser Arg Asn Thr Phe His Pro Met Pro Asp Ser Cys
            420                 425                 430
Gln Trp Pro Glu Lys Met Arg Phe Leu Asn Leu Ser Ser Thr Gly Ile
            435                 440                 445
Arg Val Val Lys Thr Cys Ile Pro Gln Thr Leu Glu Val Leu Asp Val
            450                 455                 460
Ser Asn Asn Asn Leu Asp Ser Phe Ser Leu Phe Leu Pro Arg Leu Gln
465                 470                 475                 480
Glu Leu Tyr Ile Ser Arg Asn Lys Leu Lys Thr Leu Pro Asp Ala Ser
                485                 490                 495
Leu Phe Pro Val Leu Leu Val Met Lys Ile Arg Glu Asn Ala Val Ser
            500                 505                 510
Thr Phe Ser Lys Asp Gln Leu Gly Ser Phe Pro Lys Leu Glu Thr Leu
            515                 520                 525
Glu Ala Gly Asp Asn His Phe Val Cys Ser Cys Glu Leu Leu Ser Phe
            530                 535                 540
Thr Met Glu Thr Pro Ala Leu Ala Gln Ile Leu Val Asp Trp Pro Asp
545                 550                 555                 560
Ser Tyr Leu Cys Asp Ser Pro Pro Arg Leu His Gly His Arg Leu Gln
                565                 570                 575
Asp Ala Arg Pro Ser Val Leu Glu Cys His Gln Ala Ala Leu Val Ser
            580                 585                 590
Gly Val Cys Cys Ala Leu Leu Leu Leu Ile Leu Leu Val Gly Ala Leu
            595                 600                 605
```

-continued

```
Cys His His Phe His Gly Leu Trp Tyr Leu Arg Met Met Trp Ala Trp
            610                 615                 620
Leu Gln Ala Lys Arg Lys Pro Lys Lys Ala Pro Cys Arg Asp Val Cys
625                 630                 635                 640
Tyr Asp Ala Phe Val Ser Tyr Ser Glu Gln Asp Ser His Trp Val Glu
                645                 650                 655
Asn Leu Met Val Gln Gln Leu Glu Asn Ser Asp Pro Pro Phe Lys Leu
            660                 665                 670
Cys Leu His Lys Arg Asp Phe Val Pro Gly Lys Trp Ile Ile Asp Asn
            675                 680                 685
Ile Ile Asp Ser Ile Glu Lys Ser His Lys Thr Val Phe Val Leu Ser
690                 695                 700
Glu Asn Phe Val Arg Ser Glu Trp Cys Lys Tyr Glu Leu Asp Phe Ser
705                 710                 715                 720
His Phe Arg Leu Phe Asp Glu Asn Asn Asp Ala Ala Ile Leu Val Leu
                725                 730                 735
Leu Glu Pro Ile Glu Arg Lys Ala Ile Pro Gln Arg Phe Cys Lys Leu
            740                 745                 750
Arg Lys Ile Met Asn Thr Lys Thr Tyr Leu Glu Trp Pro Leu Asp Glu
            755                 760                 765
Gly Gln Gln Glu Val Phe Trp Val Asn Leu Arg Thr Ala Ile Lys Ser
770                 775                 780
```

<210> SEQ ID NO 76
<211> LENGTH: 784
<212> TYPE: PRT
<213> ORGANISM: Artificial Sequence
<220> FEATURE:
<223> OTHER INFORMATION: human TLR2

<400> SEQUENCE: 76

```
Met Pro His Thr Leu Trp Met Val Trp Val Leu Gly Val Ile Ile Ser
1               5                   10                  15
Leu Ser Lys Glu Glu Ser Ser Asn Gln Ala Ser Leu Ser Cys Asp Arg
            20                  25                  30
Asn Gly Ile Cys Lys Gly Ser Ser Gly Ser Leu Asn Ser Ile Pro Ser
        35                  40                  45
Gly Leu Thr Glu Ala Val Lys Ser Leu Asp Leu Ser Asn Asn Arg Ile
    50                  55                  60
Thr Tyr Ile Ser Asn Ser Asp Leu Gln Arg Cys Val Asn Leu Gln Ala
65                  70                  75                  80
Leu Val Leu Thr Ser Asn Gly Ile Asn Thr Ile Glu Glu Asp Ser Phe
                85                  90                  95
Ser Ser Leu Gly Ser Leu Glu His Leu Asp Leu Ser Tyr Asn Tyr Leu
            100                 105                 110
Ser Asn Leu Ser Ser Ser Trp Phe Lys Pro Leu Ser Ser Leu Thr Phe
        115                 120                 125
Leu Asn Leu Leu Gly Asn Pro Tyr Lys Thr Leu Gly Glu Thr Ser Leu
    130                 135                 140
Phe Ser His Leu Thr Lys Leu Gln Ile Leu Arg Val Gly Asn Met Asp
145                 150                 155                 160
Thr Phe Thr Lys Ile Gln Arg Lys Asp Phe Ala Gly Leu Thr Phe Leu
                165                 170                 175
Glu Glu Leu Glu Ile Asp Ala Ser Asp Leu Gln Ser Tyr Glu Pro Lys
            180                 185                 190
```

```
Ser Leu Lys Ser Ile Gln Asn Val Ser His Leu Ile Leu His Met Lys
        195                 200                 205

Gln His Ile Leu Leu Glu Ile Phe Val Asp Val Thr Ser Ser Val
    210                 215                 220

Glu Cys Leu Glu Leu Arg Asp Thr Asp Leu Asp Thr Phe His Phe Ser
225                 230                 235                 240

Glu Leu Ser Thr Gly Glu Thr Asn Ser Leu Ile Lys Lys Phe Thr Phe
                245                 250                 255

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
        275                 280                 285

Leu Asn Gly Val Gly Asn Phe Arg Ala Ser Asp Asn Asp Arg Val Ile
    290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
                325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
        355                 360                 365

Glu Asn Leu Met Val Glu Glu Tyr Leu Lys Asn Ser Ala Cys Glu Asp
    370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
                405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
        435                 440                 445

His Ser Val Thr Gly Cys Ile Pro Lys Thr Leu Glu Ile Leu Asp Val
    450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
                485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
        515                 520                 525

Glu Ala Gly Gly Asn Asn Phe Ile Cys Ser Cys Glu Phe Leu Ser Phe
    530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
                565                 570                 575

Asp Val Arg Leu Ser Val Ser Glu Cys His Arg Thr Ala Leu Val Ser
            580                 585                 590

Gly Met Cys Cys Ala Leu Phe Leu Leu Ile Leu Leu Thr Gly Val Leu
        595                 600                 605
```

-continued

| | | | | | | | | | | | | | | |
|---|---|---|---|---|---|---|---|---|---|---|---|---|---|---|
| Cys | His 610 | Arg | Phe | His | Gly | Leu 615 | Trp | Tyr | Met | Lys | Met 620 | Met | Trp | Ala | Trp |
| Leu 625 | Gln | Ala | Lys | Arg | Lys 630 | Pro | Arg | Lys | Ala | Pro 635 | Ser | Arg | Asn | Ile | Cys 640 |
| Tyr | Asp | Ala | Phe | Val 645 | Ser | Tyr | Ser | Glu | Arg 650 | Asp | Ala | Tyr | Trp | Val 655 | Glu |
| Asn | Leu | Met | Val 660 | Gln | Glu | Leu | Glu | Asn 665 | Phe | Asn | Pro | Pro | Phe 670 | Lys | Leu |
| Cys | Leu | His 675 | Lys | Arg | Asp | Phe | Ile 680 | Pro | Gly | Lys | Trp | Ile 685 | Ile | Asp | Asn |
| Ile | Ile 690 | Asp | Ser | Ile | Glu | Lys 695 | Ser | His | Lys | Thr | Val 700 | Phe | Val | Leu | Ser |
| Glu 705 | Asn | Phe | Val | Lys | Ser 710 | Glu | Trp | Cys | Lys | Tyr 715 | Glu | Leu | Asp | Phe | Ser 720 |
| His | Phe | Arg | Leu | Phe 725 | Asp | Glu | Asn | Asn | Asp 730 | Ala | Ala | Ile | Leu | Ile 735 | Leu |
| Leu | Glu | Pro | Ile 740 | Glu | Lys | Lys | Ala | Ile 745 | Pro | Gln | Arg | Phe | Cys 750 | Lys | Leu |
| Arg | Lys | Ile 755 | Met | Asn | Thr | Lys | Thr 760 | Tyr | Leu | Glu | Trp | Pro 765 | Met | Asp | Glu |
| Ala | Gln | Arg 770 | Glu | Gly | Phe | Trp 775 | Val | Asn | Leu | Arg | Ala 780 | Ala | Ile | Lys | Ser |

HUMANIZED ANTI-S100A9 ANTIBODY AND USES THEREOF

CROSS-REFERENCE TO RELATED APPLICATIONS

The present application is a U.S. National Phase of International Application No. PCT/CA2016/050810, filed on Jul. 11, 2016, the content of which is hereby incorporated by reference in its entirety.

FIELD

The present description relates to an inhibitor of Toll-like Receptor 2 (TLR2) that specifically blocks an interaction between S100A9 and Toll-like Receptor 2 (TLR2).

BACKGROUND

Arthritis is a chronic syndrome characterized by the inflammation of peripheral joints. There is a wide spectrum of disease severity and many patients run a course of intermittent relapses and remissions with an overall pattern of slowly progressive joint destruction and deformity. Persistent inflammation produces symptoms and damages tissue causing loss of cartilage, erosion of bone matter and subluxation of the joint. This results in a high degree of morbidity resulting in disturbed daily life of the patient. Diagnosis of arthritis is typically carried out by determination of rheumatoid factors in the blood and radiological changes in peripheral joints.

Primary treatments of arthritis include first line drugs for control of pain and inflammation classified as non-steroidal anti-inflammatory drugs (NSAIDs), e.g., aspirin, ibuprofen, naproxen, methotrexate, etc. Secondary treatments include corticosteroids, slow acting antirheumatic drugs (SAARDs) or disease modifying drugs (DMs), e.g., penicillinamine, cyclophosphamide, gold salts, azothioprine, levamisole, methotrexate, etc.

All of the above-mentioned products have a variety of toxic side effects and most of them are cytotoxic. These drugs have limited advantages and their effects are mainly of short term duration. The side effects they produce, e.g., gastric erosion, and adverse effects on the kidneys and liver, dictate against their use over extended periods of time. Further the products primarily used are costly and have low benefit-risk ratios.

There still remains a need for alternative therapies, methods, compositions or compounds for the modulation of inflammatory reactions which are moderate in cost, safe, efficient and which eliminate the need for traditional products and their associated side effects, particularly over prolonged daily use.

SUMMARY

It is therefore provided an inhibitor of Toll-like Receptor 2 (TLR2) that specifically blocks an interaction between S100A9 and Toll-like Receptor 2 (TLR2).

In an embodiment, the inhibitor is an antibody that specifically binds to an epitope of S100A9 protein.

In another embodiment, the inhibitor is adapted to inhibit binding of said S100A9 protein to TLR2.

In a further embodiment, the inhibitor of TLR2 is an anti-S100A9 antibody.

In a supplemental embodiment, the anti-S100A9 antibody is a mouse antibody.

In a further embodiment, the anti-S100A9 antibody is humanized.

In another embodiment, the anti-S100A9 antibody comprises an epitope binding fragment selected from the group consisting of: Fv, F(ab'), or F(ab')2.

In an embodiment, the antibody comprises an epitope binding to C-terminal region or the hinge region of the S100A9 protein.

In a further embodiment, the antibody comprises an epitope binding to the 10 last amino acids of the C-terminal region of the S100A9 protein.

In a further embodiment, the antibody comprises an epitope binding single chain antibody.

In another embodiment, the antibody recognizes a unique epitope on the S100A9 molecule defined as LGxxTx (SEQ ID NO: 70).

In another embodiment, the epitope is defined as LGExTP (SEQ ID NO: 71).

In another embodiment, the epitope is defined as PGLGExTP (SEQ ID NO: 72).

In another embodiment, the epitope is defined as PGLGEGTP (SEQ ID NO: 67).

In an embodiment, the antibody comprises a chain selected from the group consisting of: SEQ ID NO: 2, 21, 22, 23, 25 and 41.

In an embodiment, the antibody comprises selected from the group consisting of: SEQ ID NO: 2 and 25.

In another embodiment, the antibody comprises an amino acid sequence selected from the group consisting of SEQ ID NO: 42, 43, 44, 45, 46, 47 and 48.

It is also provided an antibody comprising a chain selected from the group consisting of: SEQ ID NO: 2, 21, 22, 23, 25 and 41.

In an embodiment, the antibody comprises a chain selected from the group consisting of: SEQ ID NO: 2 and 25.

It is further provided an antibody comprising amino acid sequence of SEQ ID NO: 42; an antibody comprising amino acid sequence of SEQ ID NO: 43; an antibody comprising amino acid sequence of SEQ ID NO: 44; an antibody comprising amino acid sequence of SEQ ID NO: 45; an antibody comprising amino acid sequence of SEQ ID NO: 46; an antibody comprising amino acid sequence of SEQ ID NO: 47; and/or an antibody comprising amino acid sequence of SEQ ID NO: 48.

It is additionally provided a composition comprising the inhibitor described herein, or the antibody described herein, and a physiologically or pharmaceutically acceptable excipient.

In another embodiment, the composition is for treating an inflammatory condition.

It is further provided the use of the inhibitor described herein, the antibody provided herein, or the composition described herein, for treating an inflammatory condition.

It is additionally provide the use of the inhibitor described herein, the antibody described herein, or the composition described herein, in the manufacture of for treating an inflammatory condition.

It is also provided a method for treating an inflammatory condition comprising the step of administering to a subject in need thereof an effective amount of the inhibitor described herein, the antibody provided herein, or the composition described herein.

In an embodiment, the inflammatory condition is selected from the group consisting of: rheumatoid arthritis, asthma, gout, type I diabetes, Crohn's disease, lupus erythematosus, multiple sclerosis, inflammatory bowel disease (IBD), ulcerative colitis, chronic inflammation, auto-inflammatory syndromes, psoriasis, and cancer metastasis.

In another embodiment, the inflammatory condition is a chronic inflammatory disease. The chronic inflammatory disease includes, but not restricted to, pyogenic arthritis, pyoderma gangrunosum, acnea syndrome, adult-onset Still's disease, and systemic-onset juvenile idiopathic arthritis.

In another embodiment, the inflammatory condition is rheumatoid arthritis.

In a further embodiment, the antibody is administered to a mammal.

In another embodiment, the mammal is a human.

In an additional embodiment, the antibody is administered subcutaneously, intravenously, intramuscularly, intra-articular or intraperitoneally The terms "inhibition" or "inhibiting" as used herein is intended to mean reducing a reaction, such as an inflammatory reaction or condition. The inhibition can be preferably a treatment.

The terms "inflammatory condition" as used herein means, without being limited thereto: rheumatoid arthritis, asthma, gout, type I diabetes, Crohn's disease, lupus erythematosus, multiple sclerosis, inflammatory bowel disease (IBD), ulcerative colitis, chronic inflammation and psoriasis, auto-inflammatory diseases, etc. The inflammatory condition encompassed herein also means a chronic inflammatory disease. The chronic inflammatory disease includes, but not restricted to, pyogenic arthritis, pyoderma gangrunosum, acnea syndrome, adult-onset Still's disease, and systemic-onset juvenile idiopathic arthritis.

"Treatment" as used herein includes systemic use for the alleviation, amelioration or control of inflammation, e.g. of inflammatory rheumatic or rheumatoid disease, process, condition or event. It also includes intervention for the alleviation, amelioration or control of the sequelae or symptoms of inflammation, for example degeneration (e.g. of cells, epithelia or tissues), or especially swelling, exudation or effusion, or pain. In this context the term "treatment" is further to be understood as embracing use to reverse, restrict or control progression of any specified disease, process, condition, event or the like, including use for disease modifying effect. If any of the mentioned diseases, processes, conditions or events is associated with pain, the term "treatment" preferably encompasses the alleviation, amelioration or control (including temporal or permanent removal) of at least one further sequela or symptom in addition to pain, such as swelling, effusion, exsudation, stiffness, lack of flexibility of joints, or degeneration, more preferably of all symptoms and most preferably of the total clinical picture of the respective disease, irritation or manifestation.

DETAILED DESCRIPTION

Figure 1:
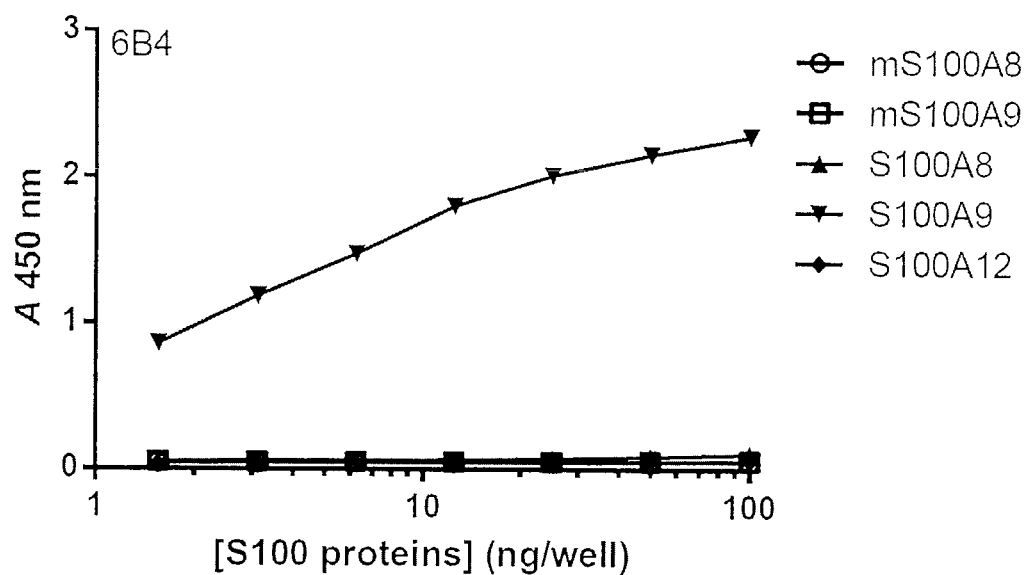
FIG. 1 illustrates the specificity of monoclonal 6B4 against human and mouse S100A9 protein. Recombinant human and murine S100A proteins (1 to 1000 ng in 100 µl) and purified human calprotectin were loaded in high-binding 96-well plates to perform standard ELISA

It is provided herein an inhibitor of Toll-like Receptor 2 (TLR2) that specifically blocks an interaction between S1009A and Toll-like Receptor 2 (TLR2).

An aspect is to provide an antibody that specifically blocks an interaction between S100A9 and Toll-like Receptor 2 (TLR2).

A further aspect is provided by an antibody that specifically binds to an epitope on S100A9 protein, said epitope being involved in interaction with Toll-like Receptor 2 (TLR2).

In a further aspect, there is provided an antibody that is adapted to inhibit binding of S100A9 protein to TLR2.

Toll-like Receptor 2 (TLR2) is a member of the toll-like receptors family and plays a role in the immune system. TLR2 is a membrane protein which is expressed on the surface of certain cells and recognizes foreign substances. Engagement of TLR2 leads to the activation of NF-κB and AP-1, contributing to the secretion of cytokines like IL-1, TNF and IL-6 linked to autoimmune disease such as rheumatoid arthritis, lupus, and Crohn's disease, to name a few.

Therapeutic compounds disclosed herein include, but are not limited to, antibodies (including fragments, analogs and derivatives thereof) binding to the S100A9 protein (including fragments, analogs and derivatives thereof and anti-idiotypic antibodies). Particularly, the antibody specifically blocks an interaction between the S100 protein and Toll-like Receptor 2 (TLR2). More particularly, the antibody specifically binds to an epitope on S100A9 protein, this epitope being involved in interaction with Toll-like Receptor 2 (TLR2). Still, most particularly, the antibody is adapted to inhibit binding of the S100 protein to TLR2.

In particular, the antibody is an anti-S100A9 antibody.

In an alternative embodiment, the interaction of the antibody with the S100 protein is dependent on the presence of $Ca^{+2}$ and/or $Zn^{+2}$ in the S100 protein.

S100A9, also known as calgranulin B and myeloid related protein-14 (MRP-14), is a calcium- and zinc-binding protein that belongs to the S100 protein family. S100A9 is highly expressed by the myeloid cell lineage and is found in the extracellular milieu during inflammatory conditions. S100A9 forms heterodimers with S100A8, another member of the S100 family. However, S100A9 may also form monomers which executes specific functions. Human S100A9 has a molecular mass of about 13 kDa and is composed of 114 amino acid residues. The S100A8/A9 protein can bind to endothelium through the interaction of S100A9 with heparan sulphate proteoglycans or of the S100A8/A9 complex with carboxylated N-glycans exclusively expressed by endothelial cells after inflammatory activation.

S100A9 proteins are arranged as noncovalently bonded homodimers. In addition, in the presence of calcium, S100A8 and S100A9 form a noncovalent heterodimer called S100A8/A9 or calprotectin, presumed to be involved in the cellular control of calcium concentrations.

S100A9 proteins are secreted and found in the serum and at inflammatory sites of patients with auto-immune diseases. S100A9 stimulate neutrophil and monocyte migration to inflammatory sites by activating the β2 integrin Mac-1, allowing these cells to adhere to and migrate across endothelial cells (Anceriz et al., 2007, Biochemical and biophysical research communications, 354: 84-89). S100A9 also induces the secretion of cytokines such as TNFα, IL-1β, and IL-6 by human monocytes and primed neutrophils by activating NF-κB and the inflammasome (Simard et al., 2013, PloS one 8: e72138).

S100A9 is a potent inducer of phagocytosis, degranulation and a mild inducer of reactive oxygen species production by neutrophils and monocytes (Simard et al., 2013, PloS one 8: e72138). S100A9 also induces cytokine secretion such as MIP-1α, RANTES, MCP-1, IL-6 and TNFα by monocytes by activating NF-κB and the inflammasome (Simard et al., 2013, PloS one 8: e72138). Cytokines such as TNFα would in turn stimulate neutrophils to release more S100A9, thereby creating a self-perpetuating cycle. S100a9$^{-/-}$ mice are resistant to adjuvant-induced arthritis and systemic lupus erythematosus, due at least in part to reduced CD8 T cell activation (Loser et al., 2010, Nature medicine, 16: 713-717). Moreover, mAbs against S100A9 prevent inflammation and joint destruction in the collagen-induced arthritis model (Cesaro et al., 2012, PloS one 7: e45478). This is associated with reduced leukocyte migration to the inflammatory sites and secretion of TNFα and IL-6. Murine S100A9 induces the release of nitric oxide (NO) by bone marrow-derived dendritic cells (Riva et al., 2012, Immunology, 137: 172-182) and macrophages (Pouliot et al., 2008, J Immunol, 181: 3595-3601). These data indicate that S100A9 promotes inflammation by enhancing phagocyte migration and inducing the secretion of pro-inflammatory cytokines, as well as the release of tissue-degrading enzymes and ROS.

It is disclosed herein that administration of antibodies against the S100A9 protein can be an effective treatment against inflammatory conditions, particularly rheumatoid arthritis.

In a further aspect, the present disclosure provides a composition comprising the antibody described herein in admixture with a physiologically or pharmaceutically acceptable excipient.

A further aspect, it is provided a method for treating an inflammatory condition comprising the step of administering to a subject in need thereof an effective amount of: the antibody as defined herein or the composition as herein defined.

In a further aspect, there is provided a method of immunotherapy comprising the step of administering to subject in need thereof an effective amount of: the antibody as herein defined or the composition as defined herein.

In a further aspect, it is provided a method for treating a TLR-2 neurodegenerative diseases comprising the step of administering to subject in need thereof an effective amount of: the antibody as defined herein or the composition as defined herein.

A further aspect provides a method for diagnosing or treating an TLR-2-associated condition in a cell, tissue, organ or animal comprising the step of administering to said cell, tissue, organ or animal in need thereof an effective amount of: the antibody as defined herein or the composition as defined herein.

Humanized antibodies and antibodies from non-human species whose protein sequences have been modified to increase their similarity to antibody variants produced naturally in humans. Humanization can be necessary when the process of developing a specific antibody involves generation in a non-human immune system (such as that in mice). Antibody humanization methods are designed to produce a molecule with minimal immunogenicity when applied to humans, while retaining the specificity and affinity of the parental non-human antibody. The protein sequences of antibodies produced in this way are partially distinct from homologous antibodies occurring naturally in humans, and are therefore potentially immunogenic when administered to human patients.

Humanization has played a fundamental role in the remarkable progress of antibodies as therapeutic reagents. In vitro discovery of human antibodies via enrichment technologies such as phage display or immunization of transgenic mice bearing the antibody human gene repertoire have provided powerful means to generate human antibodies.

More particularly, the antibody specifically binds to an epitope on S100A9, this epitope blocking the interaction with Toll-like Receptor 2 (TLR2). Still, most particularly, the antibody inhibits binding of the S100 protein to TLR2. Still, most particularly, the antibody blocks the activation of the TLR2.

In a particular embodiment, the antibody comprises an epitope binding fragment that is selected from: Fv and/or F(ab') and/or F(ab')2. In particular, the antibody comprises an epitope-binding single chain antibody.

In a particular embodiment, the antibody bears an epitope that overlaps with the region of the S100 protein that interacts with TLR2. Particularly, the antibody recognizes a unique epitope on the S100A9 molecule defined as: LGxxTx (SEQ ID NO: 70). More particularly, the epitope is defined as LGExTP (SEQ ID NO: 71) or PGLGExTP (SEQ ID NO: 72) or PGLGEGTP (SEQ ID NO: 67).

In a particular embodiment, the antibody comprises a chain selected from: SEQ ID NO: 2, 21, 22, 23, 25, or 41; more particularly SEQ ID NO: 2, or 25.

The anti-S100 Ab described herein may be employed in admixture with a suitable physiological or pharmaceutical carrier. Such compositions comprise a therapeutically effective amount of the antibody, and a physiologically or a pharmaceutically acceptable carrier or excipient. Such a carrier includes but is not limited to saline, buffered saline, dextrose, water, glycerol, ethanol, and combinations thereof. The formulation should suit the mode of administration.

An antibody as defined herein, acting as inhibitor or antagonist of S100 protein, can be administered alone or in combination with other antibodies directed toward other complementary targets, including but not limited to, other S100 polynucleotides or polypeptides.

In accordance with the present disclosure, there is provided a method and composition for the treatment of inflammatory conditions.

It is described herein that myeloid-related proteins (MRP) play a role in the process of neutrophil migration to inflammatory site.

The antibodies can be used to treat, inhibit or prevent diseases, disorders or conditions associated with aberrant expression and/or activity of a polypeptide encompassed herein, including, but not limited to, any one or more of the inflammatory diseases, disorders, or conditions described herein. The treatment and/or prevention of inflammatory diseases, disorders, or conditions associated with expression and/or activity of the anti-S100 protein includes, but is not limited to, alleviating symptoms associated with those diseases, disorders or conditions. Anti-S100 antibodies can be provided in pharmaceutically acceptable compositions as known in the art or as described herein.

A summary of the ways in which the antibodies described herein may be used therapeutically includes binding S100 polypeptides locally or systemically in the body or by direct cytotoxicity of the antibody, e.g. as mediated by complement (CDC) or by effector cells (ADCC). Some of these approaches are described in more detail below.

The antibodies encompassed herein may be advantageously utilized in combination with other monoclonal or chimeric antibodies, or with lymphokines. The antibodies may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient, is preferred. Thus, in a preferred embodiment, human antibodies, fragments, derivatives, analogs, or nucleic acids, are administered to a human or animal patient for therapy or prophylaxis.

It is preferred to use high affinity and/or potent in vivo inhibiting and/or neutralizing antibodies against S100 polypeptides or polynucleotides encompassed herein, fragments or regions thereof, for therapy of disorders related to S100 polynucleotides or polypeptides, including fragments thereof. Such antibodies, fragments, or regions, will preferably have an affinity for S100 polynucleotides or polypeptides encompassed herein, including fragments thereof.

Inhibition or reduction of the activity of S100 polynucleotides or polypeptides may be useful in treating diseases, disorders, and/or conditions of the immune system, by inhibiting the proliferation, differentiation, or mobilization (chemotaxis) of immune cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, anti-S100 Ab can be used as a marker or detector of a particular immune system disease or disorder.

Similarly, allergic reactions and conditions, such as asthma (particularly allergic asthma) or other respiratory problems, may also be treated, prevented, and/or diagnosed by inhibitors of S100 polynucleotides or polypeptides, or antagonists of S100 polynucleotides or polypeptides. Moreover, these molecules can be used to treat anaphylaxis, hypersensitivity to an antigenic molecule, or blood group incompatibility.

Inhibition of S100 protein can be achieved by using antibodies that bind or block access to the S100 protein to a binding site or to any activation site activated by it. Particularly, the binding site or activation site is the TLR-2 (toll-like receptor 2) present on many cells.

The antibodies against S100 (i.e. S100A9) can be employed to inhibit chemotaxis and activation of macrophages and their precursors, and of neutrophils, basophiles, B lymphocytes and some T cell subsets, e.g., activated and CD8+ cytotoxic T cells and natural killer cells, in autoimmune and chronic inflammatory and infective diseases. Examples of auto-immune diseases include rheumatoid arthritis, multiple sclerosis, and insulin-dependent diabetes. Some infectious diseases include silicosis, sarcoidosis, idiopathic pulmonary fibrosis caused by preventing the recruitment and activation of mononuclear phagocytes, idiopathic hyper-eosinophilic syndrome caused by preventing eosinophil production and migration, endotoxic shock caused by preventing the migration of macrophages and their production of the chemokine polypeptides encompassed herein. Examples of chronic inflammation include hypercalprotectinemia and auto-inflammatory syndromes. The antagonists may also be used for treating atherosclerosis, by preventing monocyte infiltration in the artery wall.

The anti-S100 Ab may also be used to treat inflammation by preventing the attraction of monocytes to a wound area. They may also be used to regulate normal pulmonary macrophage populations, since acute and chronic inflammatory pulmonary diseases are associated with sequestration of mononuclear phagocytes in the lung.

The anti-S100 Ab may also be used to treat rheumatoid arthritis by preventing the attraction of monocytes into synovial fluid in the joints of patients. Neutrophil and monocyte influx and activation play a significant role in the pathogenesis of both degenerative and inflammatory arthropathies.

The anti-S100 Ab may be used to interfere with the deleterious cascades attributed primarily to IL-1 and TNF, which prevents the biosynthesis of other inflammatory cytokines. In this way, the antagonists may be used to prevent inflammation. The antagonists may also be used to inhibit prostaglandin-independent fever induced by S100 chemokines.

Alternatively, the anti-S100 Ab can be used in conjunction with IL-10, which is involved in the down regulation of neutrophil migration at an inflamed site, such as for example, but without limiting it to, Crohn's disease or ulcerative colitis.

The anti-S100 Ab can also be used to treat cases of bone marrow failure, for example, aplastic anemia and myelodysplastic syndrome. The anti-S100 Ab can alternatively be used to treat or prevent graft rejection. The anti-S100 Ab may also be used to treat asthma and allergy by preventing eosinophil accumulation in the lung. The antagonists may be employed in a composition with a pharmaceutically acceptable carrier, e.g., as hereinafter described.

Particularly, there is provided a method for treating an inflammatory condition comprising the step of administering to a subject in need thereof an effective amount of: the antibody as defined herein or the composition as defined herein.

Particularly, the inflammatory condition may be selected from: rheumatoid arthritis, asthma, gout, type I diabetes, Crohn's disease, lupus erythematosus, multiple sclerosis, inflammatory bowel disease (IBD), ulcerative colitis, chronic inflammation, psoriasis, or cancer metastasis. More particularly, the inflammatory condition is rheumatoid arthritis. In another embodiment, the inflammatory condition is a chronic inflammatory disease. The chronic inflammatory disease includes, but not restricted to, pyogenic arthritis, pyoderma gangrunosum, acnea syndrome, adult-onset Still's disease, and systemic-onset juvenile idiopathic arthritis.

Alternatively, there is provided a method of immunotherapy comprising the step of administering to subject in need thereof an effective amount of: the antibody as defined herein or the composition as defined herein.

In an alternative embodiment, it is provided a method for treating a TLR-2 neurodegenerative diseases comprising the step of administering to subject in need thereof an effective amount of: the antibody or the composition, both as defined herein. Particularly, the TLR-2 neurodegenerative disease is: Parkinsons' disease or Alzeihmer's disease.

Alternatively, it is provided a method for diagnosing or treating an TLR-2-associated condition in a cell, tissue, organ or animal comprising the step of administering to said cell, tissue, organ or animal in need thereof an effective amount of: the antibody or the composition, both as defined herein.

In another embodiment, there are provided antibody-based therapies that involve administering antibodies specific to S100 proteins to an animal, preferably a mammal, and most preferably a human patient for treating one or more of the disclosed diseases, disorders, or conditions.

Particularly, the antibody as defined herein is administered subcutaneously, intravenously, intramuscularly, intra-articularly or intraperitoneally.

EXAMPLES

Example 1

Production of the Mouse Monoclonal Antibody 6B4

Female BALB/c mice (4 wk old) were immunized by i.p. injections with 30 µg of purified recombinant S100A9 in 50

µl of endotoxin-free PBS (Sigma-Aldrich) mixed in an equal volume of complete Freund's adjuvant. Antibody responses were enhanced by injections 14 days later with S100A9 using incomplete Freund's adjuvant, and final boost was given on day 28 with proteins alone. On day 31, spleen cells from the immunized mice were fused with SP2 murine myeloma cells and cultured in hypoxanthine/amethopterin/thymidine selection medium.

Figure 2:
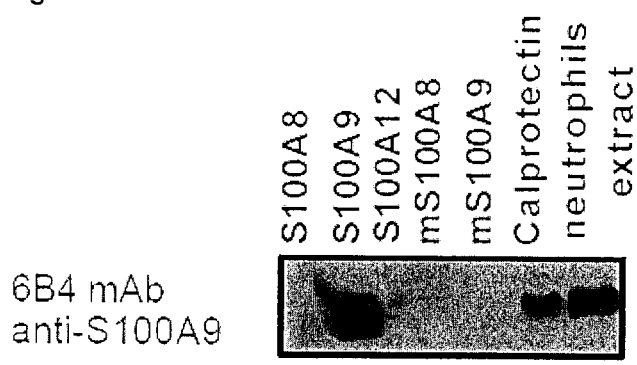
FIG. 2 illustrates the specificity of monoclonal 6B4 against human S100A8, S100A9 and S100A12 proteins. Recombinant S100A8, S100A9, S100A12, mS100A8 (murine S100A8), mS100A9 (murine S100A9), purified human calprotectin and neutrophil's crude extract were loaded onto SDS-PAGE (15%), transferred on nitrocellulose membranes and detected by western blotting using, 6B4 mAb.

Culture supernatants of the hybridomas were screened by ELISA using plates coated with 1 µg/ml recombinant proteins in 0.1 M carbonate buffer (pH 9.6). Positive hybridoma cells were cloned by limiting dilution. The mAb clone 6B4 showed the most distinctive recognition of the recombinant protein S100A9 and was isotyped as IgG1 kappa. Specificity of the 6B4 mAb was confirmed by ELISA and Western blot analysis (FIGS. 1 and 2)

Example 2

Humanization of the Mouse Monoclonal Antibody 6B4

The murine 6B4 mAb was humanized using in silico modeling within the complementarity-determining region (CDR)-grafting paradigm. The following steps have been carried out:

3D Modeling of the Variable Regions of the Mouse 684 Monoclonal Antibody.

Figure 5A:
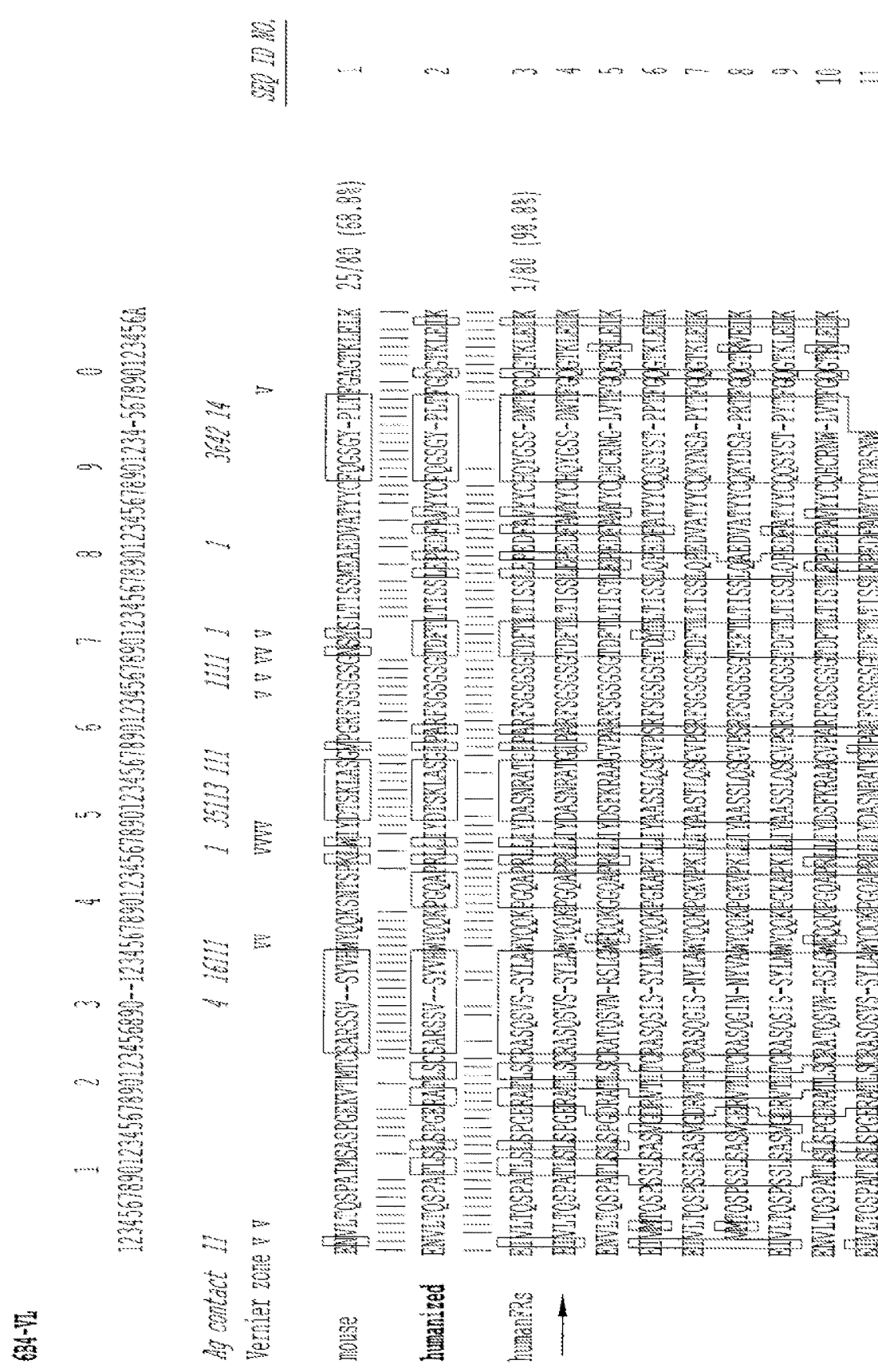
FIG. 5A, continuing on FIG. 5B, FIG. 5C and FIG. 5D, illustrate an alignment of the sequences of the V domains of the light chain of mouse and humanized 6B4 antibodies.
Figure 5B:
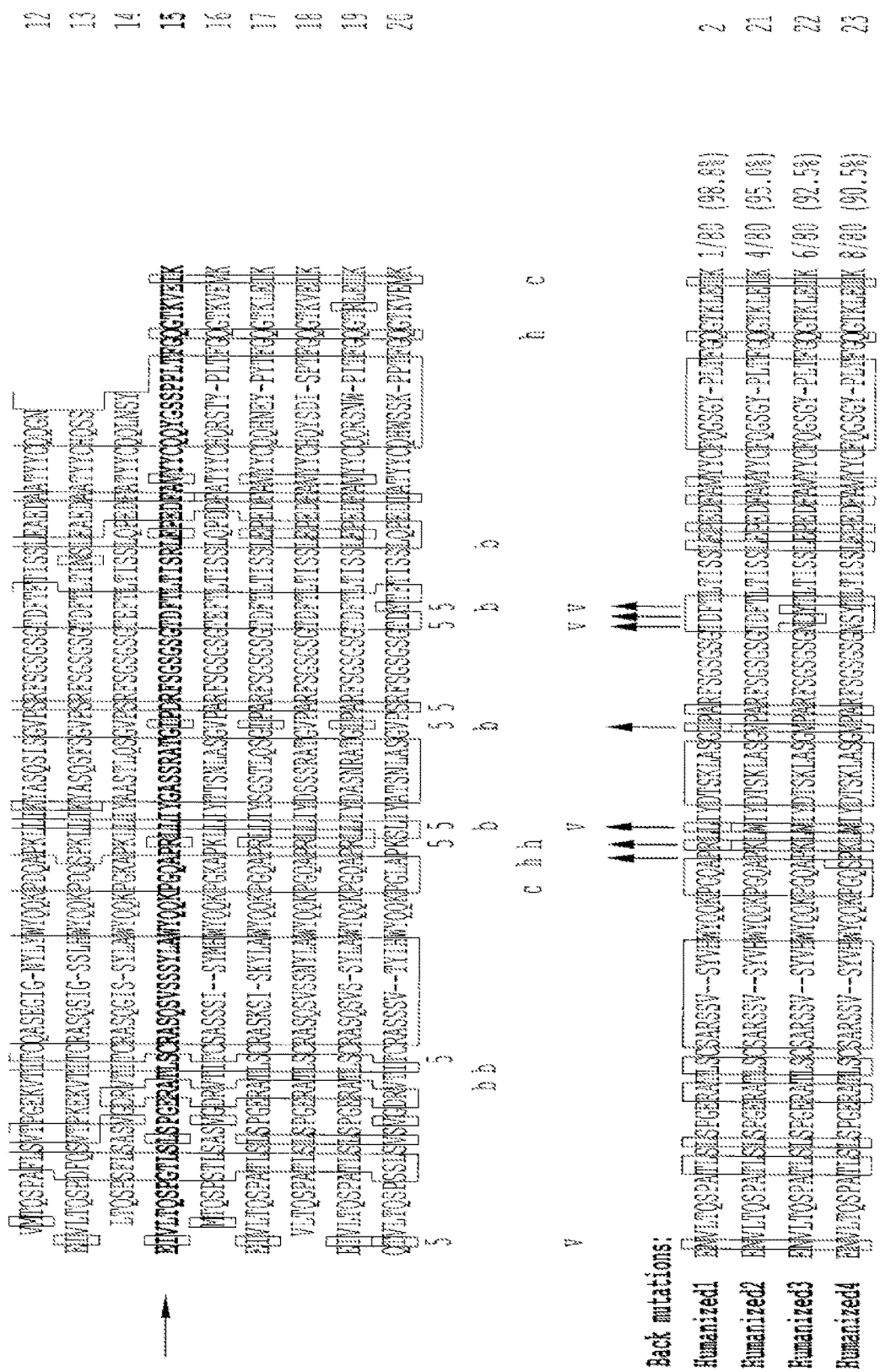
Figure 5D:
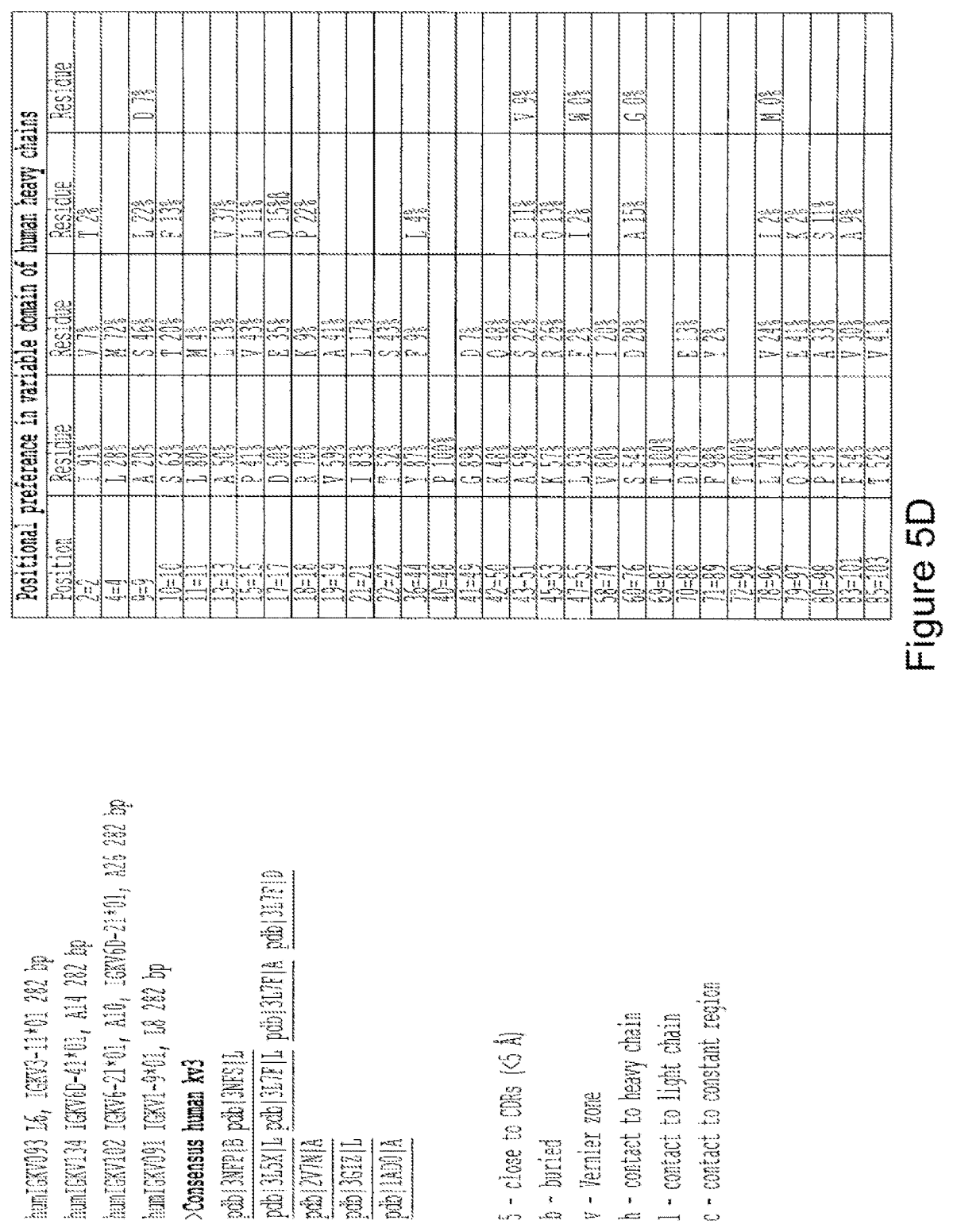

This task was accomplished by homology modeling. The most similar template structures to the murine 6B4 variable sequences were identified by a BLAST search against PDB (protein databank). To build an initial model of the mouse 6B4 variable region the following template structures were used (PDB codes): 1QOK (chain A) for the light chain, and 1I3G (chain H) for the heavy chain. Other suitable templates can be found in the PDB entry 1SY6, 3IXY, 2W9D, 3NCY, 3I50 and 1FIG for the light chain, and in the PDB entries 1H8S, 2NTF, 1CIC, 1H8N and 1Z3G for the heavy chain. Required mutations were operated on these template structures according to the murine 6B4 sequences: 15 mutations in the 1QOK light chain, and 18 mutations in the 1I3G heavy chain. The mutated structures corresponding to the heavy and light chains of the murine 6B4 variable domains were assembled into two-chain antibody structures by superimposing the heavy and light chains of the respective template structures. The resulting structure of the assembled 6B4 variable domain was first refined by energy minimization with the AMBER force-field and a stepwise release of constraints, ranging from the CDR loops that were relaxed first, to the backbone heavy atoms of the framework region that were fully relaxed only in the last stage. The CDR-H3 loop in each antibody variable domain structure was then refined by Monte-Carlo-minimization (MCM) conformational sampling, in which dihedral angles in the CDR-H3 region were sampled in each MCM cycle followed by energy minimization of a predefined region extending 10 Å around the initial conformation of the CDR-H3 loop. A representation of the modeled variable region of the mouse 6B4 antibody is given in FIG. 3 (left panel and see alignment in FIG. 5). The structures of the human or humanized variable sequences most similar to each of the 6B4 variable sequences were also identified from PDB, and then superimposed onto the modeled structures of the murine 6B4 variable domains. These structures include PDB entries 3NFP, 1AD0, 3L5X, 2V7N and 3GIZ for the light chain, and PDB entries 1I9R, 3NFP, 1UJ3, 3GKW and 1WT5 for the heavy chain. These structures were used to assist in the modeling of mutations in the framework region in order to build humanized 3D-structures starting from the modeled murine 3D-structure.

Characterization of the Mouse 684 Amino-Acid Sequences and Modeled Structure.

This step was carried out to estimate the humanness index, antigen contact propensity index, to delineate the CDRs, canonical residues, inter-chain packing (VH/VL interface residues), variable-/constant-region packing (VH/CH and VL/CL interface residues), unusual framework residues, potential N- and O-glycosylation sites, buried residues, Vernier zone residues, and proximity to CDRs. Internet-available resources and local software were used to assess these properties.

Selection of the Best Human Light-Chain and Heavy-Chain Frameworks for the Mouse CDRs.

Figure 6A:
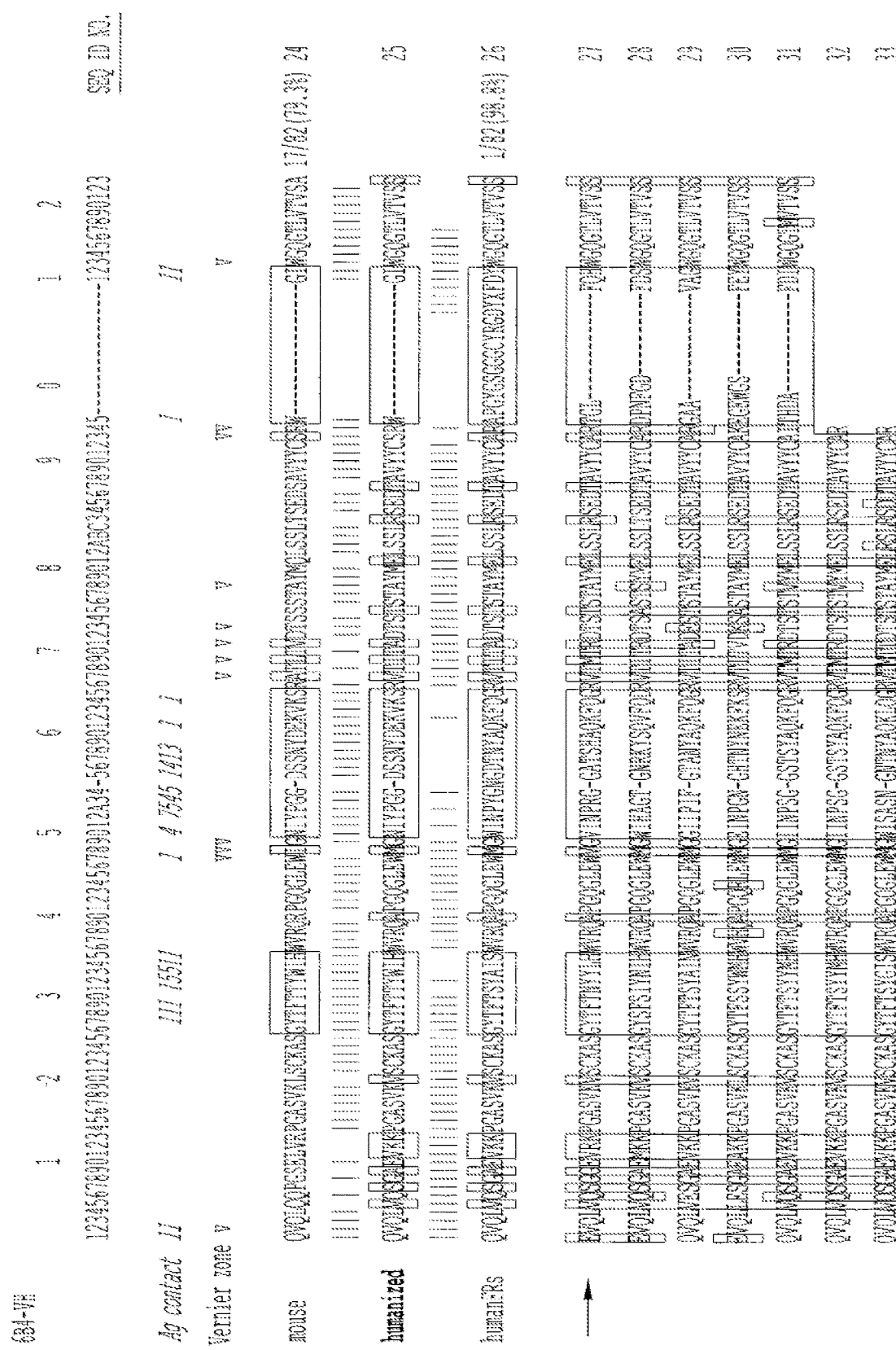
FIG. 6A, continuing on FIG. 6B and FIG. 6C, illustrates an alignment of the sequences of the V domains of the heavy chain of mouse and humanized 6B4 antibodies.
Figure 6B:
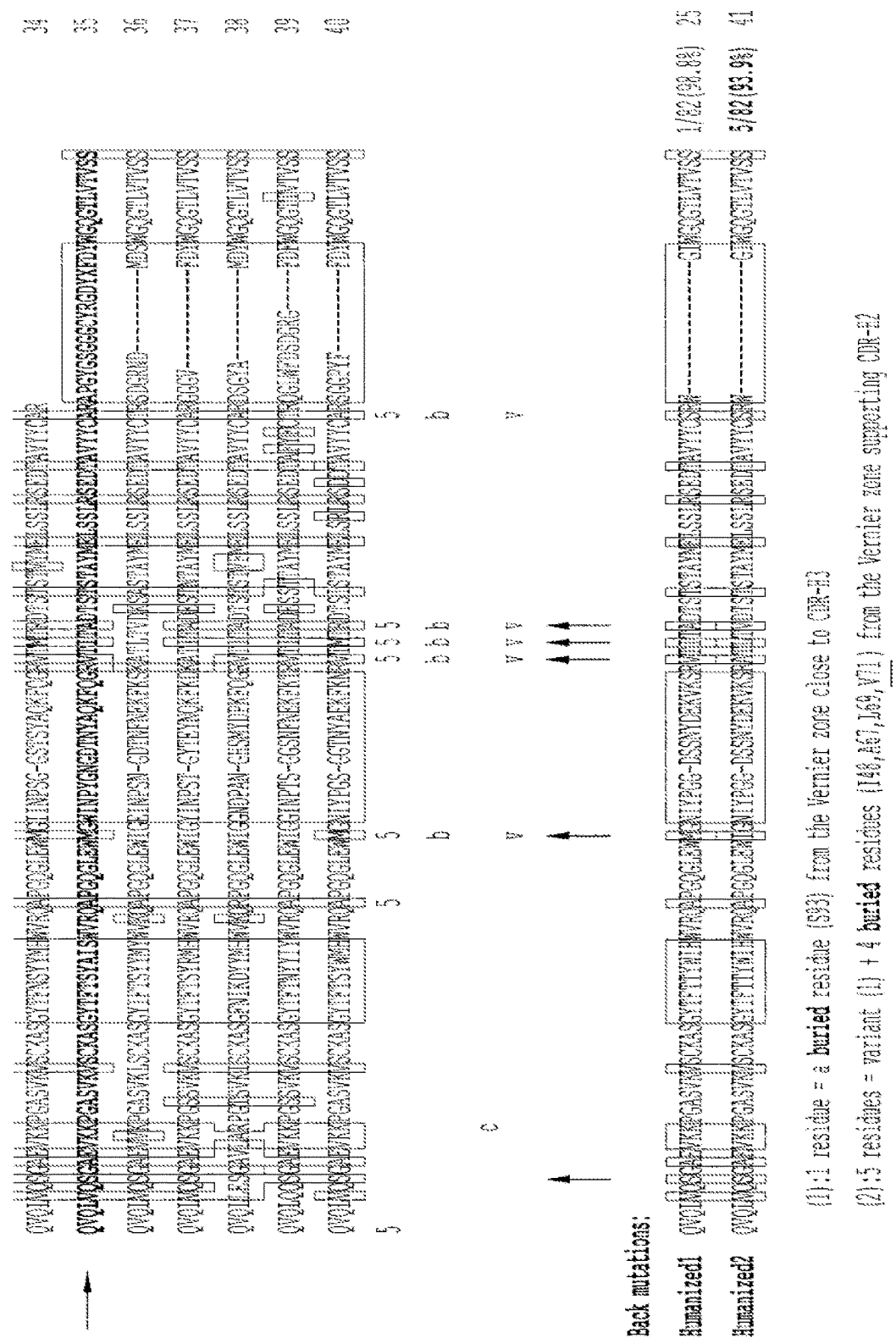

This was done by standard sequence homology comparison against a local copy of human germline databases (VBASE), against other sequence libraries (Genbank and SwissProt), as well as the set of human framework consensus sequences. BLAST searches were conducted to retrieve sequence matches with highest homology in the framework region only (thus excluding CDRs) while matching the length of the CDR loops. The human frameworks identified for the light and heavy chains of the 6B4 antibody correspond to the κ3 and h1 classes, respectively. Several human germline framework sequences that are most similar to the 6B4 framework sequences were retained in addition to the human consensus sequences for these classes (see the alignments in FIGS. 5 and 6).

Identification of Framework Residues for Back-Mutations and Design of Multiple Humanized Variants.

This is an important step that flags amino-acid residues that should be mutated to the corresponding human sequences with particular care. These residues represent primary candidates for back-mutations to the mouse sequences in case of affinity loss. It relies on the identification of residues in one or more of the following categories: canonical, CDR-H3, Vernier zone, unusual, CDR-proximal (within 5 Å), inter-chain packing, and glycosylation-site residues. Such residues might affect antigen-binding site and affinity directly or indirectly. The antigen contact propensity index as well as amino-acid occurrence in human germline databases at each position are also extremely important in deciding whether a certain residue can be safely mutated from the mouse sequence to the human sequence. The light chain of the 6B4 antibody requires 26 mutations to its proposed humanized framework for 100% framework humanization. The heavy chain of the 6B4 antibody requires 18 mutations to its proposed humanized framework for 100% framework humanization. The most advanced humanized 6B4 sequences display 98.8% humanization to their respective closest human frameworks (see the alignments in FIGS. 5 and 6), and are labelled 6B4-VL_humanized-1 (SEQ ID NO: 2) and 6B4-VH_humanized-1 (SEQ ID NO: 25). Additional humanized sequences were also designed in which additional several residues from the 6B4 mouse sequences were retained based on careful structural and comparative sequence analyses that indicate a high probability of altering antigen-binding affinity if mutations are to be introduced at these positions. These sequences are labelled 6B4-VL_humanized-2 (SEQ ID NO: 21), 6B4-VL_humanized-3 (SEQ ID NO: 22), 6B4-VL_humanized-4 (SEQ ID NO: 23), 6B4-VH_humanized-2 (SEQ ID NO: 41). The 4 humanized light-chain and 2 humanized heavy-chain sequences can be assembled into 8 humanized antibodies.

6B4 Light (Kappa) Chain Humanized Variant 1
(SEQ ID NO: 42)
MVLQTQVFISLLLWISGAYGE*NVLTQSPATLSLSPGERATLSCSARSSVS*

*YVHWYQQKPGQAPRLLIYDTSKLASGIPARFSGSGSGTDFTLTISSLEPE*

*DFAVYYCFQGSGYPLTFGQGTKLEIK*RTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

6B4 Light (Kappa) Chain Humanized Variant 2
(SEQ ID NO: 43)
MVLQTQVFISLLLWISGAYGE*NVLTQSPATLSLSPGERATLSCSARSSVS*

*YVHWYQQKPGQAPKLWIYDTSKLASGVPARFSGSGSGTDFTLTISSLEPE*

*DFAVYYCFQGSGYPLTFGQGTKLEIK*RTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

6B4 Light (Kappa) Chain Humanized Variant 3
(SEQ ID NO: 44)
MVLQTQVFISLLLWISGAYGE*NVLTQSPATLSLSPGERATLSCSARSSVS*

*YVHWYQQKPGQAPKLWIYDTSKLASGVPARFSGSGSGNDYTLTISSLEPE*

*DFAVYYCFQGSGYPLTFGQGTKLEIK*RTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

6B4 Light (Kappa) Chain Humanized Variant 4
(SEQ ID NO: 45)
MVLQTQVFISLLLWISGAYGE*NVLTQSPATLSLSPGERATLSCSARSSVS*

*YVHWYQQKPGQSPKLWIYDTSKLASGVPARFSGSGSGNSYTLTISSLEPE*

*DFAVYYCFQGSGYPLTFGQGTKLEIK*RTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

6B4 Heavy (Igg4) Chain Humanized Variant 1
(SEQ ID NO: 46)
MDWTWRILFLVAAATGTHA*QVQLVQSGAEVKKPGASVKVSCKASGYTFT T*

*YWIHWVRQAPGQGLEWMGNIYPGGDSSNYDEKVKSRVTITADTSTSTAYM*

*ELSSLRSEDTAVYYCSRWGIWGQGTLVTVSS*ASTKGPSVFPLAPCSRSTS

ESTAALGCLVKDYFPEPVTVSWNSGALTSGVHTFPAVLQSSGLYSLSSVV

TVPSSSLGTKTYTCNVDHKPSNTKVDKRVESKYGPPCPSCPAPEFLGGPS

VFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQPEN

NYKTTPPVLDSDGSFFLYSRLTVDKSRWQEGNVFSCSVMHEALHNHYTQK

SLSLSLGK

6B4 Heavy (Igg4) Chain Humanized Variant 2
(SEQ ID NO: 47)
MDWTWRILFLVAAATGTHA*QVQLVQSGAEVKKPGASVKVSCKASGYTFTT*

*YWIHWVRQAPGQGLEWIGNIYPGGDSSNYDEKVKSRATLTVDTSTSTAYM*

*ELSSLRSEDTAVYYCSRWGIWGQGTLVTVSS*ASTKGPSVFPLAPCSRSTS

ESTAALGCLVKDYFPEPVTVSWNSGALTSGVHTFPAVLQSSGLYSLSSVV

TVPSSSLGTKTYTCNVDHKPSNTKVDKRVESKYGPPCPSCPAPEFLGGPS

VFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQPEN

NYKTTPPVLDSDGSFFLYSRLTVDKSRWQEGNVFSCSVMHEALHNHYTQK

SLSLSLGK

6B4 Heavy (Igg4) Chain Chimeric
(SEQ ID NO: 48)
MDWTWRILFLVAAATGTHA*QVQLQQPGSELVRPGASVKLSCKASGYTFTT*

*YWIHWVRQRPGQGLEWIGNIYPGGDSSNYDEKVKSRATLTVDTSSSTAYM*

*QLSSLTSEDSAVYYCSRWGIWGQGTLVTVSA*ASTKGPSVFPLAPCSRSTS

ESTAALGCLVKDYFPEPVTVSWNSGALTSGVHTFPAVLQSSGLYSLSSVV

TVPSSSLGTKTYTCNVDHKPSNTKVDKRVESKYGPPCPSCPAPEFLGGPS

VFLFPPKPKDTLMISRTPEVTCVVVDVSQEDPEVQFNWYVDGVEVHNAKT

KPREEQFNSTYRVVSVLTVLHQDWLNGKEYKCKVSNKGLPSSIEKTISKA

KGQPREPQVYTLPPSQEEMTKNQVSLTCLVKGFYPSDIAVEWESNGQPEN

NYKTTPPVLDSDGSFFLYSRLTVDKSRWQEGNVFSCSVMHEALHNHYTQK

SLSLSLGK

Signal sequence in black (human)
*Variable region in italics (humanized or mouse)*
Constant region in bold (human)

Figure 3:
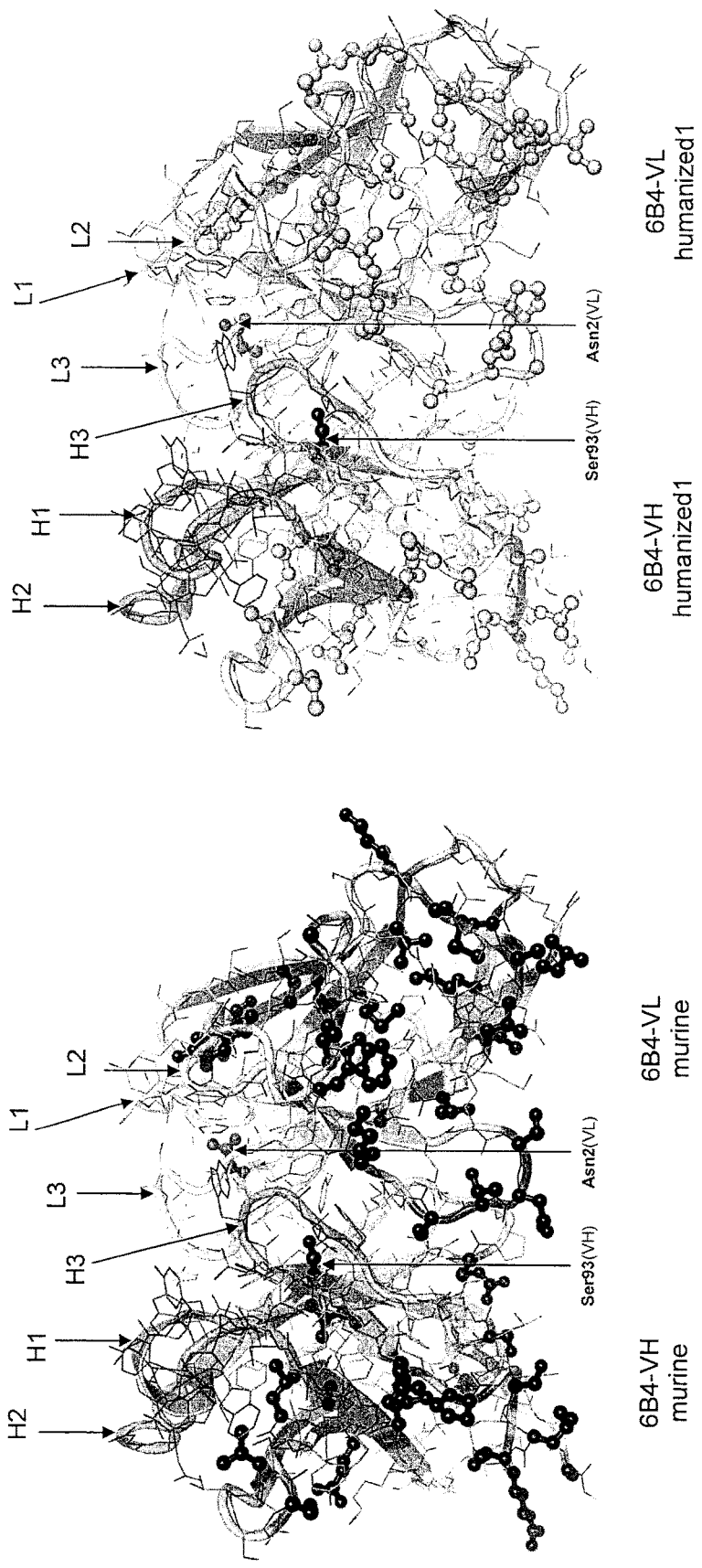
FIG. 3 illustrates molecular models for the mouse and humanized variant-1 of 6B4 variable domains. Replaced framework residues are shown with ball-and-stick models. Mouse residues retained in the humanized antibody are labeled and shown with ball-and-stick models. CDR loops are labeled (H1, H2, H3, L1, L2, L3) in the heavy chain and in the light chain.

The molecular model of the 6B4-VL_humanized-1 (SEQ ID NO: 2): 6B4-VH_humanized-1 (SEQ ID NO: 25) pair, constructed by homology modeling starting from the 3D model of the murine 6B4 variable region, is depicted in FIG. 3 (right panel).

In the case of light-chain 6B4-VL_humanized-2 sequence (SEQ ID NO: 21), framework residues Trp-L47, Lys-L45 and Val-L58 were additionally retained from the mouse sequence since residue Trp-L47 is part of the Vernier zone supporting CDR-L2 and mutation to Leu may be problematic for the conformation of this loop, and residues Lys-L45 and Val-L58 are in direct contact with Trp-L47 and may have to be mutated together with this residue. Residues Trp-L47 and Val-L58 are buried and should not be immunogenic, while residue Lys-L45 is close to the CDR-H3. Also, Lys at position 45 and Val at position 58 occur in human frameworks.

The light-chain 6B4-VL_humanized-3 sequence (SEQ ID NO: 22) is based on the 6B4-VL_humanized-2 sequence and adds two back-mutations to introduce the murine residues Asn-L69 and Tyr-L71, which are part of the Vernier zone supporting CDR-L1, with Tyr-L71 being partially buried and having antigen binding propensity.

The light-chain 6B4-VL_humanized-4 sequence (SEQ ID NO: 23) adds another two back-mutations to 6B4-VL_humanized-3, namely Ser-L43 and Asp-L70. Mutation of residue at position 70 modifies the net charge at the surface not too far from CDR-L1. Residue Ser-L43 is in contact with the heavy chain. Ser at position 43 occurs in human frameworks.

In the case of heavy-chain 6B4-VH_humanized-2 sequence (SEQ ID NO: 41), framework residues Ile-H48, Ala-H67, Leu-H69 and Val-H71 were additionally retained from the mouse sequence, which allows restoration of four Vernier-zone residues supporting CDR-H2 that have been shown to be important in some cases for retaining antigen binding affinity of humanized antibodies. It was noted that all these residues are buries, and that Val at position 71 occurs in human frameworks.

Figure 4:
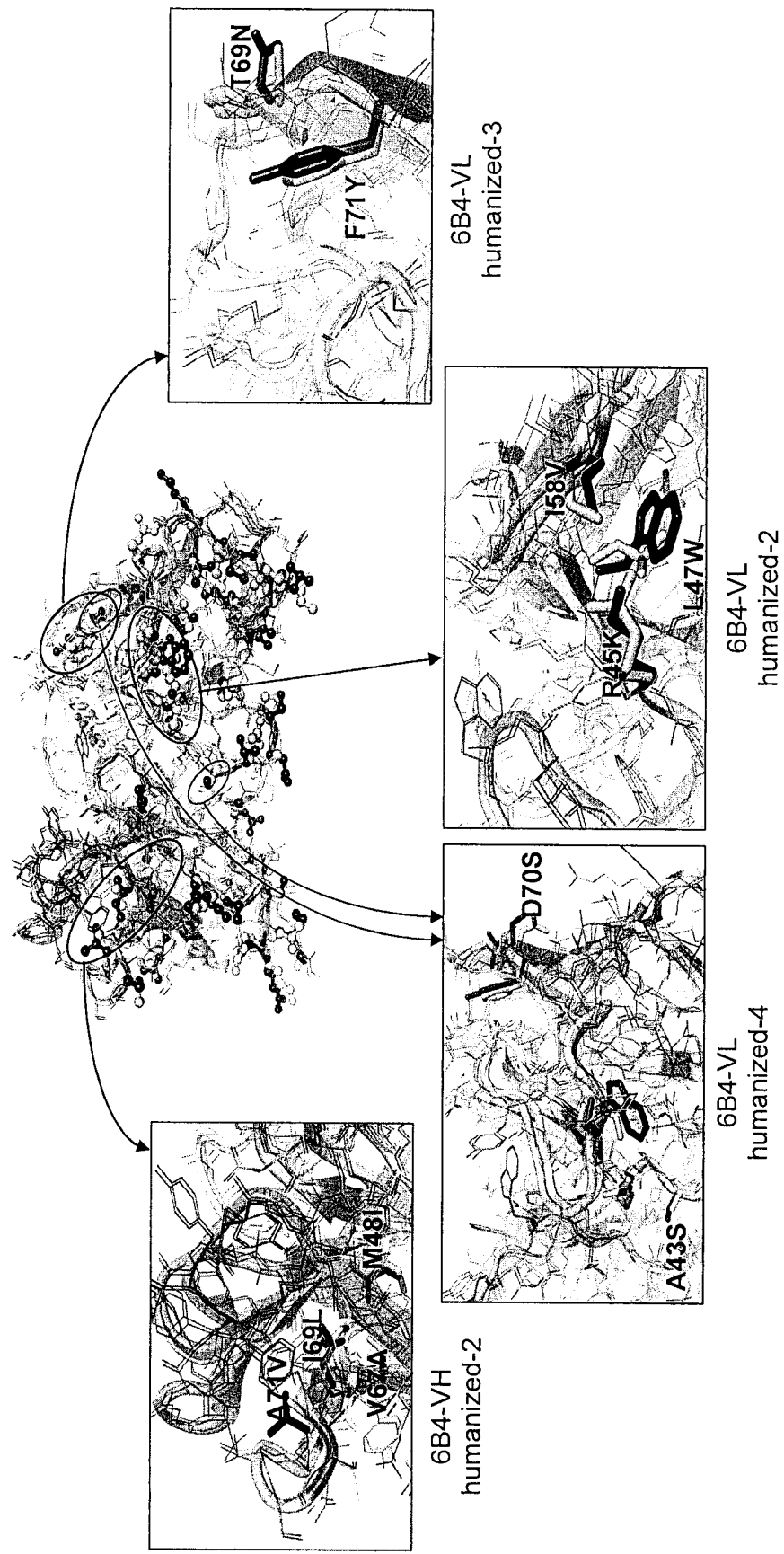
FIG. 4 illustrates overlayed models of murine and humanized 6B4 variable domains highlighting regions targeted for back-mutations. In the insets, human framework residues back-mutated to murine residues are highlighted in sticks models.

A summary and close-up views of the back-mutations corresponding to all humanized variants are provided in Table 1 and FIG. 4.

and 10 and 50 μg of S100A9 peptides were deposited on PVDF membrane. The dried membrane was then blocked with TBS/0.1% Tween/milk 5% 30 min at room temperature under gentle agitation and labelled with 1 μg/ml of 6B4 mAb for 1 hr at RT. The membrane was extensively washed with TBS/0.1% Tween, then labelled with goat anti-mouse (1/20

TABLE 1

| Variant | %-framework humanization | Charge variable domain | Number of murine residues | Back-mutations | Notes | SEQ ID NO. |
|---|---|---|---|---|---|---|
| 6B4-VL |  |  |  |  |  |  |
| Humanized-1 | 98.8 | 0 | 1 | I2N | an N-terminal semi-buried residue (N2) with antigen-contact propensity and part of Vernier zone | 2 |
| Humanized-2 | 95.0 | 0 | 4 | L47W, R45K, I58V | residue W47 is part of the Vernier zone supporting CDR-L2 and mutation to Leu may be problematic for the conformation of this loop residues 45 and 58 are in direct contact with 47 and may have to be mutated together with residue 47 residues W45 and V47 are buried, residue K45 is close to the CDR-H3 Lys at position 45 and Val at position 58 occur in human frameworks | 21 |
| Humanized-3 | 92.5 | 0 | 6 | T69N, F71Y | residues 69 and 71 are part of the Vernier zone supporting CDR-L1 residue 71 is buried and has antigen-contacting probability | 22 |
| Humanized-4 | 90.0 | 1 | 8 | A43S, D70S | mutation of residue at position 70 modifies the net charge at the surface not too far from CDR-L1 residue 43 is in contact with the heavy chain Ser at position 43 occurs in human frameworks | 23 |
| Chimeric | 68.8 | 1 | 25 | See seq. align. |  | 1 |
| 6B4-VH |  |  |  |  |  |  |
| Humanized-1 | 98.8 | 1 | 1 | A93S | a buried residue (S93) from the Vernier zone close to CDR-H3 | 25 |
| Humanized-2 | 93.9 | 1 | 5 | M48I, V67A, I69L, A71V | restoration of four Vernier zone residues supporting CDR-H2 that have been shown to be important in some cases for retaining antigen binding affinity of humanized antibodies all these residues are buried Val at position 71 occurs in human frameworks | 41 |
| Chimeric | 79.3 | 1 | 17 | See seq. align. |  | 24 |

Example 3

Localization of the Epitope Recognized by the Monoclonal Anti-S100A9 Clone 684

Three (3) regions of human S100A9 protein were chosen to start the epitope mapping; N-terminal, Hinge and C-terminal. The sequences are indicated as follows:

```
Complete sequence of human S100A9
                               (SEQ ID NO: 49)
MTCKMSQLER NIETIINTFH QYSVKLGHPD TLNQGEFKEL

VRKDLQNFLK KENKNEKVIE HIMEDLDTNA DKQLSFEEFI

MLMARLTWAS HEKMHEGDEG PGHHHKPGLG EGTP

Sequences of regions
S100A9 N-term (N)
                               (SEQ ID NO: 50)
MTCKMSQLERNI S100A9 Hinge (H)
                               (SEQ ID NO: 51)
DLQNFLKKENKNEK S100A9 C-term (C)
                               (SEQ ID NO: 52)
TWASHEKMHEGDEGPGHHHKPGLGEGTP
```

A dot blot was first performed to verify the ability of the mAb 6B4 to recognize these regions of S100A9. Briefly, 1 μg of recombinant S100A9 or S100A8 (negative control), 000) in blocking buffer for 1 hr at RT under gentle agitation. The membrane was then extensively washed and visualized by enhanced chemiluminescence (ECL) as described by the manufacturer (PerkinElmer).

The C-terminal region was then separated into 7 peptides as listed below.

```
C-term
                               (SEQ ID NO: 52)
TWASHEKMHEGDEGPGHHHKPGLGEGTP

C1
                               (SEQ ID NO: 53)
TWASHEKMH

C2
                               (SEQ ID NO: 54)
SHEKMHEGD

C3
                               (SEQ ID NO: 55)
KMHEGDEGP

C4
                               (SEQ ID NO: 56)
EGDEGPGHH

C5
                               (SEQ ID NO: 57)
EGPGHHHKP
```

```
            C6
                                          (SEQ ID NO: 58)
            GHHHKPGLG

C7
                                          (SEQ ID NO: 59)
            HKPGLGEGTP
```

Figure 7:
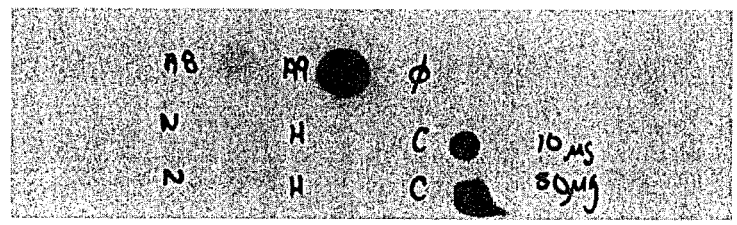
FIG. 7 illustrates that 6B4 recognizes the C-terminal peptide of S100A9. Recombinant S100A8 and S100A9 (1 µg), PBS1×, N-terminal (N), Hinge (H) and C-terminal (C) peptides (10 and 50 µg) were put onto PVDF membrane to perform dot blot analysis using the mAb 6B4.
Figure 8:
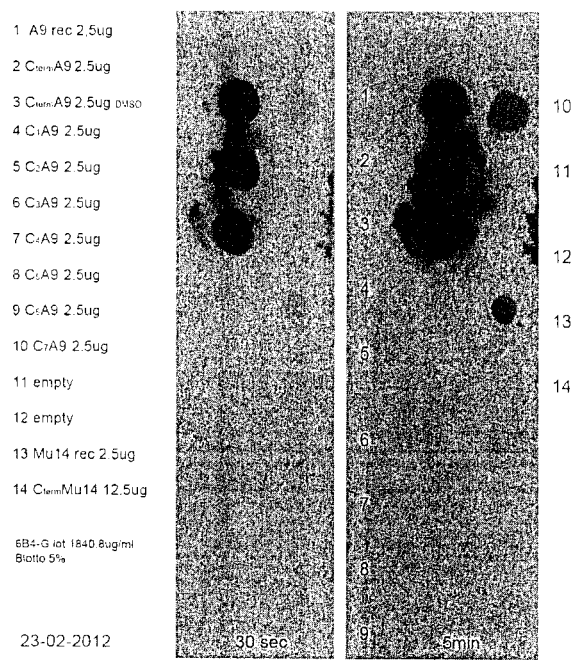
FIG. 8 illustrates that 6B4 recognizes the 10 last amino acid of the C-terminal region f S100A9 (peptide C7). 2.5 µg of recombinant S100A9, C-terminal, C1 to C7 peptides, recombinant mouse S100A9 and C-terminal of mouse S100A9 were put onto PVDF membrane to perform dot blot analysis using the mAb 6B4.

Dot blots were carried out as described above to verify which region of the C-terminal portion is recognized by 6B4 (FIGS. 7 and 8).

Figure 9:
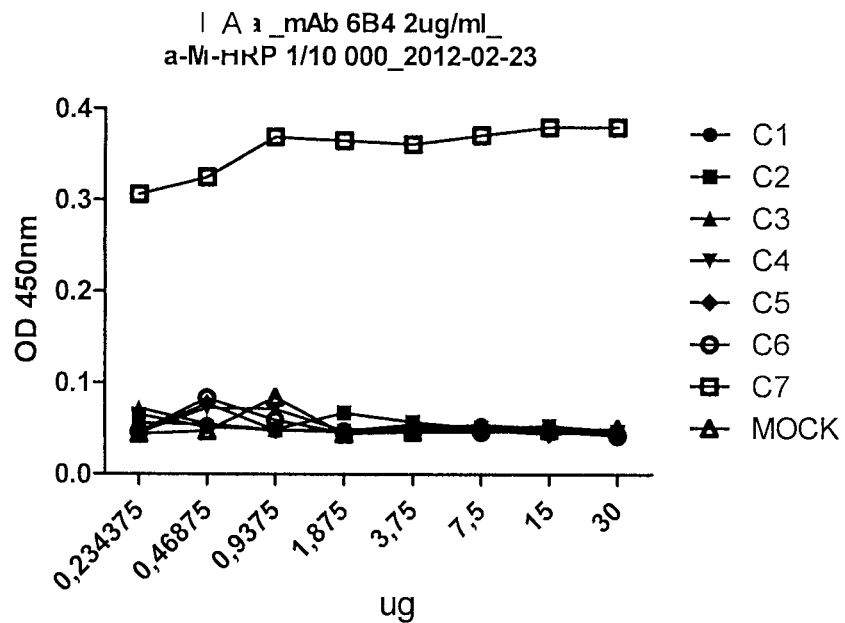
FIG. 9 illustrates that 6B4 and polyclonal anti-S100A9 recognize mostly the last 10 amino acid of the C-terminal region of S100A9 (peptide C7). 96 wells high binding plates were coated with increasing concentrations of S100A9 peptides. Non-specific binding sites were blocked with PBS/ 0.1% Tween/2% BSA and then a solution containing (A) 6B4 (2 µg/ml) or (B) pAb a-A9 (1 µg/ml) was added to the wells and incubated 1 hr at RT. After extensive washes, HRP-conjugated goat anti-mouse was added the plates and incubated 1 hr at RT. The reactions were revealed by adding TMBS and stopped with $H_2SO_4$. The optical density was read at 450 nm. 3—Other mAbs against S100A9 also bind to the C7 peptide as shown in FIG. 10.
Figure 9:
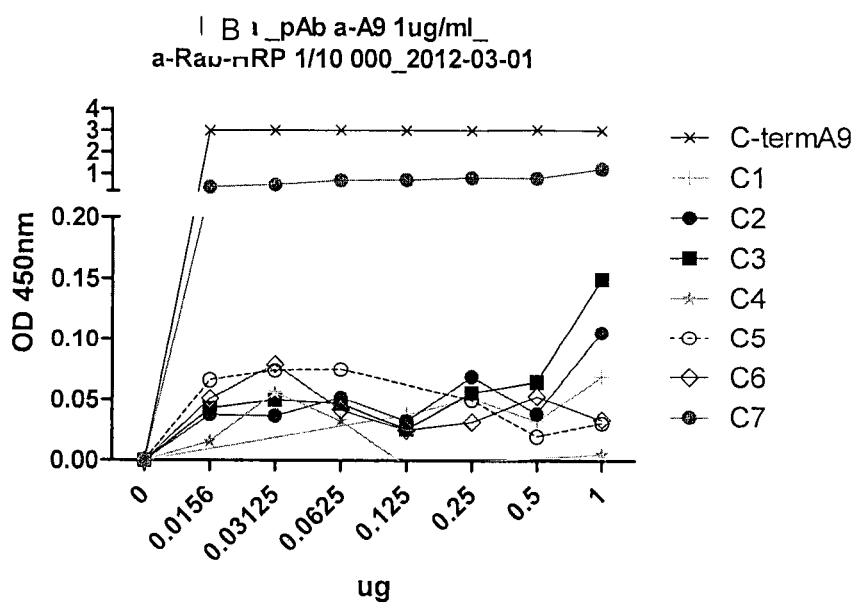

The results from dot blot assays were then confirmed by direct ELISA. Briefly, increasing concentrations of peptides were put into 96 wells high binding plate in 0.1M $NaHCO_3$, pH 9.6 overnight at 4° C. The plate was extensively washed with PBS1x/0.1% Tween and blocked with PBS1x/0.1% Tween/2% BSA 1 hr at RT. After three washes, 100 µl of a solution containing 2 µg/ml of 6B4 was added in the wells for 1 hr at RT. The plate was washed and 100 µl of a solution containing HRP conjugated goat anti-mouse (1/10000) was added to the wells for 1 hr at RT. The plate was washed and the detection was made by adding the HRP substrate (TMBS) as described by the manufacturer. The reaction was stopped by the addition of $H_2SO_4$ and read using spectrofluorometer at 450 nm (FIG. 9).

Figure 10:
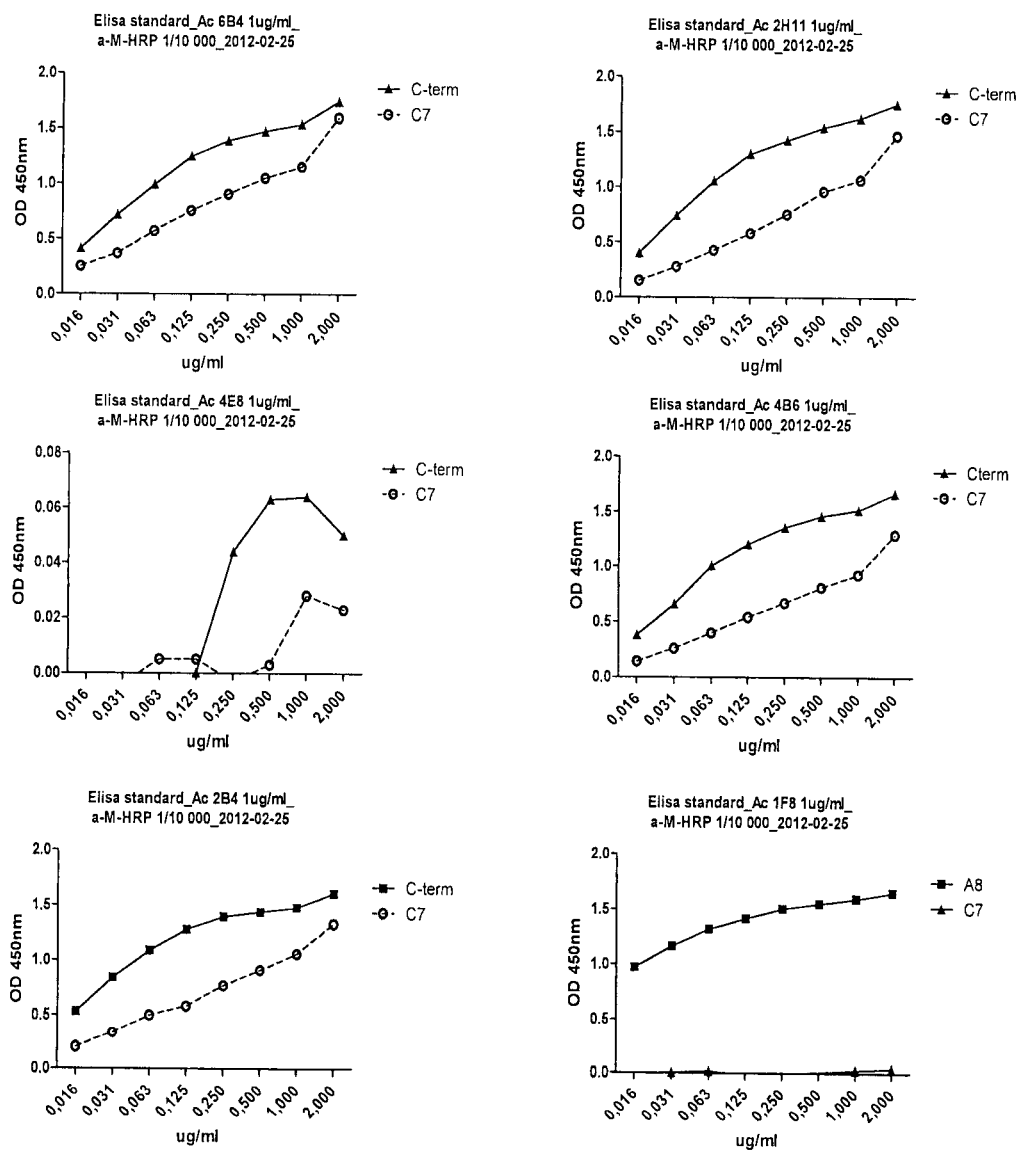
FIG. 10 illustrates that all monoclonal anti-S100A9 antibodies bind to the last 10 amino acid of the C-terminal region of S100A9 (peptide C7). 96 wells high binding plates were coated with increasing concentrations of S100A9 peptides. Non-specific binding sites were blocked with PBS/ 0.1% Tween/2% BSA and then a solution containing 1 µg/ml of 6B4, 2H11, 4E8, 4B6, 2B4 or 1F8 (anti-S100A8 used as negative control) was added to the wells and incubated 1 hr at RT. After extensive washes, HRP-conjugated goat anti-mouse was added to the plates and incubated 1 hr at RT. The reactions were revealed by adding TMBS and stopped with $H_2SO_4$. The optical density was read at 450 nm.
Figure 16:
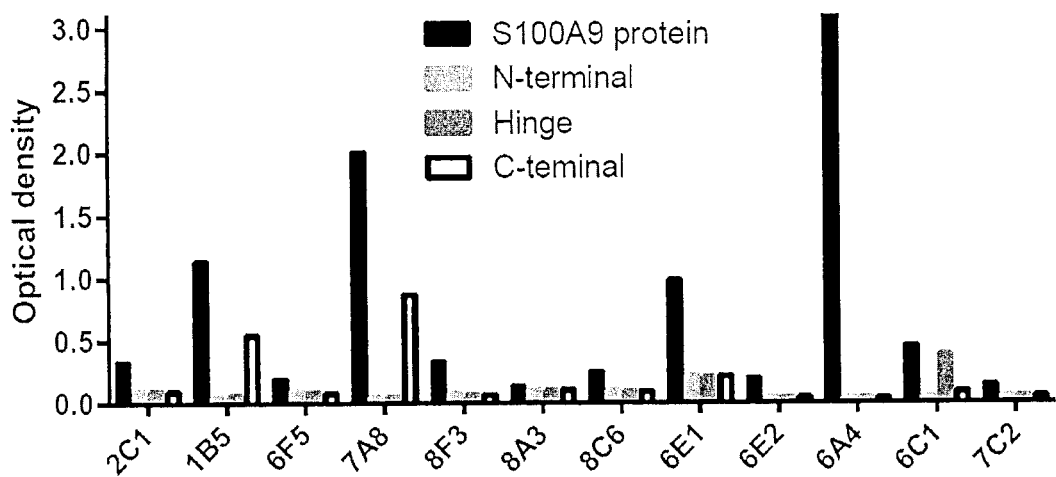
FIG. 16 illustrates blocking rabbit mAbs against recognize the hinge region or C-terminal peptide of S100A9. PBS1×, recombinant S100A9, N-terminal, Hinge and C-terminal peptides (50 ng/well) were coated in a 96 well plate. One hundred µl of cell culture supernatants of 11 blocking rabbit anti-S100A9 were added to the wells. Binding of the mAbs was revealed using a HRP-labelled goat anti-rabbit IgG antibody. mAbs 1B5 and 7A8 binds to the c-terminal region of S100A9. mAb 6C1 binds to the hinge region.

Thus, mAbs against S100A9 bind to the C7 peptide as shown in FIG. 10. As seen in FIG. 16, blocking rabbit mAbs against recognize the hinge region or C-terminal peptide of S100A9. mAbs 1B5 and 7A8 binds to the C-terminal region of S100A9. mAb 6C1 binds to the hinge region.

Figure 17:
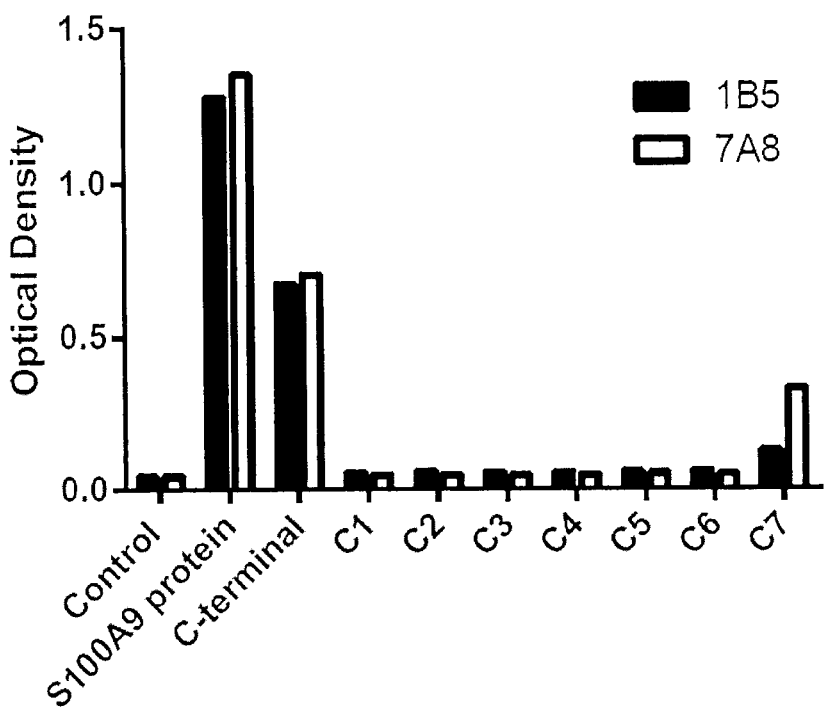
FIG. 17 illustrates that mAbs 1B5 and 7A8 bind to the 10 last amino acid of the C-terminal region of S100A9 (peptide C7). PBS1×, recombinant S100A9, C-terminal, and C1 to C7 peptides (50 ng/well) were coated in a 96 well plate. One hundred µl of cell culture supernatants of 11 blocking rabbit anti-S100A9 were added to the wells. Binding of the mAbs was revealed using a HRP-labelled goat anti-rabbit IgG antibody. Both mAbs bind to the C7 peptide.

More particularly, mAbs 1B5 and 7A8 bind to the 10 last amino acid of the C-terminal region of S100A9 (peptide C7; see FIG. 17).

The C6 and C7 regions were then separated in smaller peptides as listed below to determine the binding epitope of 6B4 mAb.

```
            C-term
                                          (SEQ ID NO: 52)
            TWASHEKMHEGDEGPGHHHKPGLGEGTP C6a
                                          (SEQ ID NO: 60)
            GPGHHHKP C6b
                                          (SEQ ID NO: 61)
            PGHHHKPG C6c
                                          (SEQ ID NO: 62)
            GHHHKPGL C6d
                                          (SEQ ID NO: 63)
            HHHKPGLG C6e
                                          (SEQ ID NO: 64)
            HHKPGLGE C6f
                                          (SEQ ID NO: 65)
            HKPGLGEG C6g
                                          (SEQ ID NO: 66)
            KPGLGEGT C7
                                          (SEQ ID NO: 59)
            HKPGLGEGTP C7a
                                          (SEQ ID NO: 67)
            PGLGEGTP C7b
                                          (SEQ ID NO: 68)
            LGEGTP C7c
                                          (SEQ ID NO: 69)
            EGTP
```

Figure 11:
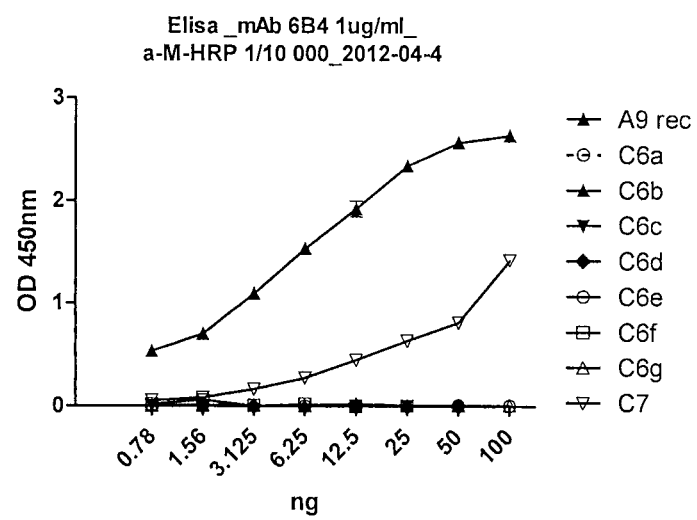
FIG. 11 illustrates that the continuous epitope recognized by 6B4 is PGLGEGTP (C7a). 96 wells high binding plates were coated with increasing concentrations of S100A9 peptides. Non-specific binding sites were blocked with PBS/ 0.1% Tween/2% BSA and then a solution containing 6B4 (1 µg/ml) was added to the wells and incubated 1 hr at RT. As negative control, some wells were incubated with PBS only (2e Ab). After extensive washes, HRP-conjugated goat anti-mouse was added in the plates and incubated 1 hr at RT. The reactions were revealed by adding TMBS and stopped with $H_2SO_4$. The optical density was read at 450 nm.
Figure 11:
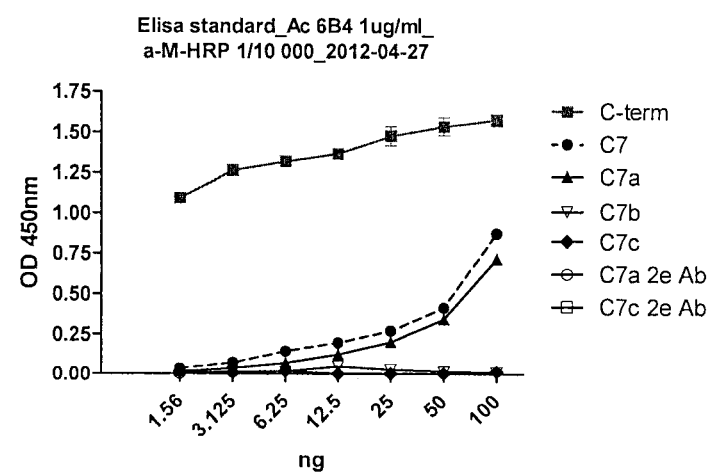
Figure 12:
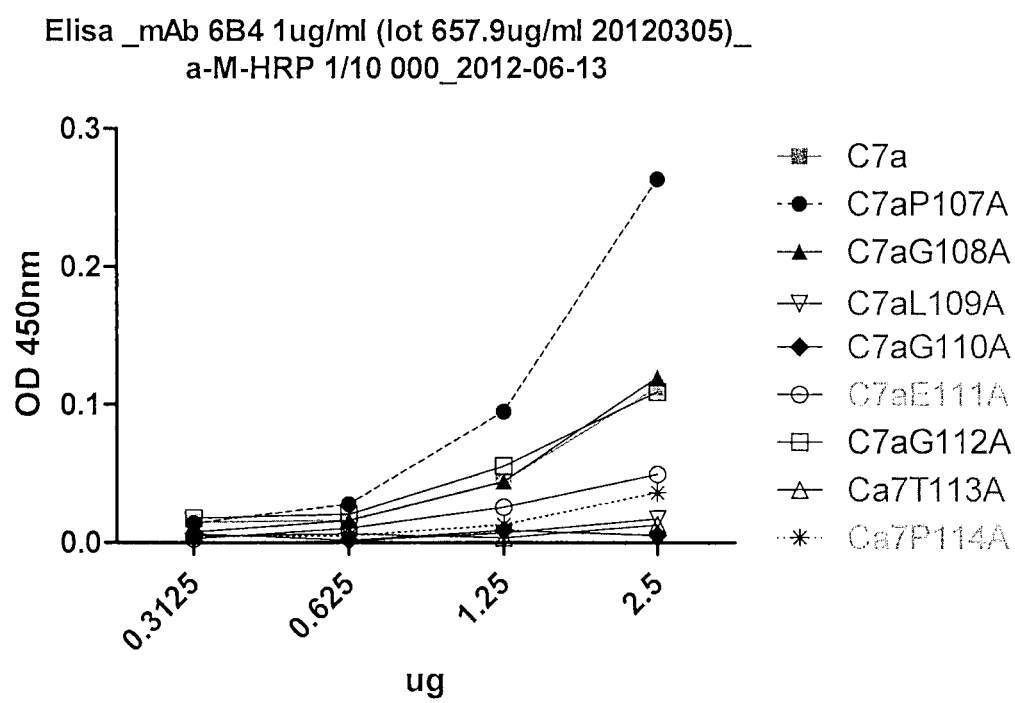
FIG. 12 illustrates that L109, G110, T113 and to a lesser extent, E111 and P114 are crucial for the binding of 6B4 to the epitope localized in the C-terminal region of S100A9. 96 wells high binding plates were coated with increasing concentrations of S100A9 peptides. Non-specific binding sites were blocked with PBS/0.1% Tween/2% BSA and then a solution containing 6B4 (1 µg/ml) was added to the wells and incubated 1 hr at RT. After extensive washes, HRP-conjugated goat anti-mouse was added in the plates and incubated 1 hr at RT. The reactions were revealed by adding TMBS and stopped with $H_2SO_4$. The optical density was read at 450 nm.

Amino acids essential to the binding of 6B4 mAb were then determined. Peptides were designed in which selected amino acids were replaced by alanine. As shown in FIG. 11, L109, G110, T113 and to a lesser extent, E111 and P114 were crucial for the binding of 6B4 to the epitope localized in the C-terminal region of S100A9. FIG. 12 shows that replacement of P107 by alanine increased the binding of 6B, whereas G108 and G112 proved non-essentials to the binding of 6B4.

The epitope sequence was therefore determined to be: PGLGEGTP (SEQ ID NO: 67), with essential amino acids in bold and an amino acid which limits binding in italics. Based on this, it can be determined that the humanized 6B4 antibody recognizes a unique epitope on the S100A9 molecule that can be defined as: LGxxTx (SEQ ID NO: 70), LGExTP (SEQ ID NO: 71) or PGLGExTP (SEQ ID NO: 72).

Figure 13:
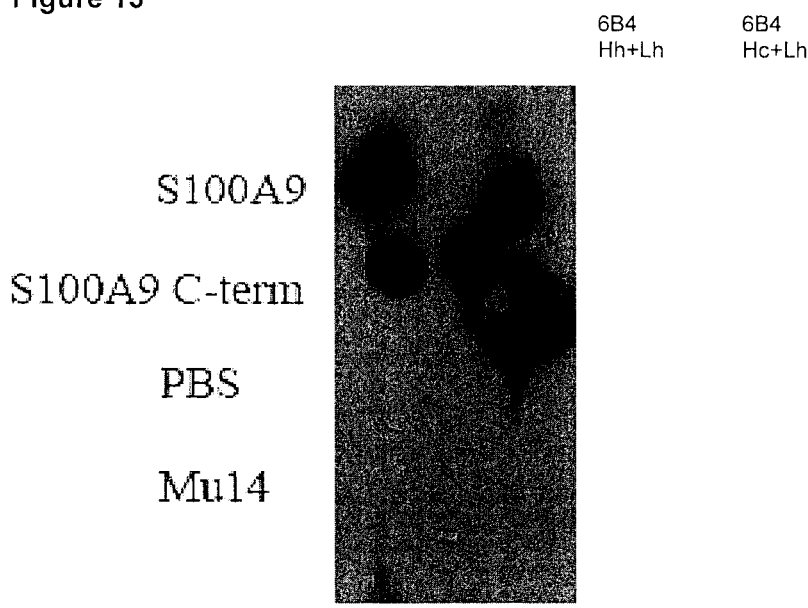
FIG. 13 illustrates that humanized 6B4 recognizes the C-terminal peptide of S100A9. Recombinant human (S100A9) mouse S100A9 (Mu14) (1 µg), PBS1×, and C-terminal S100A9 peptide (2 µg) were put onto PVDF membrane to perform dot blot analysis using the humanized 6B4 Hh+Lh or Hc+Lh.

A shown in FIG. 13, the humanized 6B4 has a similar ability to recognize S100A9 and its C-terminal region.

Example 4

Anti-S100A9 Antibodies Block Activation of TLR-2 Receptors

THP1-XBlue™ cells ($1 \times 10^5$) were pretreated with Fc block (BD Biosciences) for 10 minutes at 37° C. The cells were then incubated with increasing concentrations of S100A8 or S100A9, in presence or absence of 10 µg/ml of anti-TLR2, anti-TLR4, anti-RAGE or their respective isotopic controls for 24 h. The cells were then centrifuged and the supernatants were harvested and incubated with Quanti-Blue™, which turns purple in the presence of secreted alkaline phosphatase. Secreted alkaline phosphatase levels were determined spectrophotometrically at 650 nm.

Figure 14:
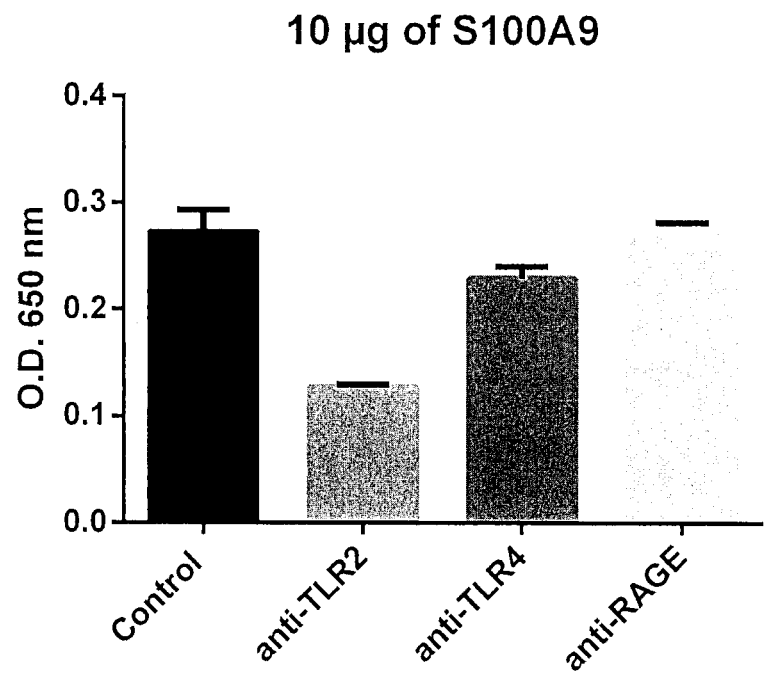
FIG. 14 illustrates that S100A9 is a ligand of TLR2. THP-Blue cells, which contain a reporter construct expressing the secreted embryonic alkaline phosphatase (SEAP) gene under the control of NF-kB and AP-1, were incubated with a neutralising anti-TLR2 (5 µg/ml), isotype-matched Abs (5 µg/ml) or PBS1× for 1 h at 37° C. and then activated with the indicated concentrations of S100A9 for 24 h at 37° C. Supernatants were then harvested and incubated with Quanti-Blue substrate as described by the manufacturer and the optical density was read at 650 nm. Results are means+/−SEM from two replicates from one experiment representative of three independent experiments.
Figure 15:
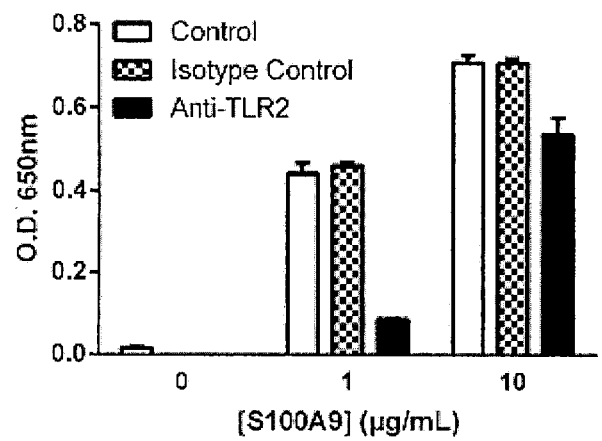
FIG. 15 illustrates that blocking antibodies against TLR2 inhibit S100A9 induced NF-κB activation in THP-blue cells. THP-Blue cells, which contain a reporter construct expressing the secreted embryonic alkaline phosphatase (SEAP) gene under the control of NF-kB and AP-1, were incubated with a neutralising anti-TLR2 (5 µg/ml), isotype-matched Abs (5 µg/ml) or PBS1× for 1 h at 37° C. and then activated with the indicated concentrations of S100A9 for 24 h at 37° C. Supernatants were then harvested and incubated with Quanti-Blue substrate as described by the manufacturer and the optical density was read at 650 nm. Results are means+/−SEM from two replicates from one experiment representative of three independent experiments.

Binding of S100A9 to TLR2 was first compared to TLR4 and RAGE, two putative receptors for these proteins. THP1-Xblue cells were stimulated with 10 µg/ml of S100A9 in presence or absence of antibodies against TLR2, TLR4 or RAGE (100 µg/ml). While anti-RAGE failed to inhibit the stimulation of THP-1blue cells, anti-TLR4 modestly inhibited the expression of the reporter gene alkaline phosphatase (FIG. 14). In contrast, anti-TLR2 reduced by approximately 50% the secretion of alkaline phosphatase in response to S100A9. This inhibition was increased to more than 85% when the ratio of antibody to stimulus was increased to 10:1, and used to stimulate the cells (1 µg/ml of S100A9, FIG. 15). As expected, concentrations lower than 40 µg/ml of S100A12 failed to stimulate THP1-Xblue cells. These results indicate that TLR2 is a major receptor for S100A9.

While the disclosure has been described in connection with specific embodiments thereof, it will be understood that it is capable of further modifications and this application is intended to cover any variations, uses, or adaptations of the invention, including such departures from the present disclosure as come within known or customary practice within the art to which the invention pertains and as may be applied to the essential features hereinbefore set forth, and as follows in the scope of the appended claims.

The invention claimed is:

1. An inhibitor of Toll-like Receptor 2 (TLR2) that specifically blocks an interaction between S1009A and Toll-like Receptor 2 (TLR2), consisting of a humanized antibody and comprises a light chain variable region comprising an amino sequence selected from the group consisting of: SEQ ID NOs: 2, 21, 22, and 23 and a heavy chain variable region comprising an amino sequence selected from the group consisting of: SEQ ID NOs: 25 and 41.

2. The inhibitor of claim 1, wherein said antibody comprises an epitope binding to the C-terminal region or the hinge region of the S100A9 protein.

3. The inhibitor of claim 1, wherein said antibody comprises an epitope binding to the 10 last amino acids of the C-terminal region of the S100A9 protein.

4. The inhibitor of claim 1, wherein said antibody recognizes a unique epitope on the S100A9 molecule defined as LGxxTx (SEQ ID NO: 70), LGExTP (SEQ ID NO: 71), PGLGExTP (SEQ ID NO: 72), or PGLGEGTP (SEQ ID NO: 67).

5. A humanized anti-S100A9 antibody comprising a light variable region comprising one amino acid sequence selected from the group consisting of: SEQ ID NOs: 2, 21, 22, and 23, and a heavy chain variable region comprising one amino acid sequence selected from the group consisting of SEQ ID NOs: 25 and 41.

6. A composition comprising the inhibitor of claim 1.

7. A method for treating rheumatoid arthritis comprising the step of administering to a subject in need thereof an effective amount of the inhibitor of claim 1.

* * * * *